United States Patent
Isobe et al.

(10) Patent No.: US 8,316,961 B2
(45) Date of Patent: Nov. 27, 2012

(54) REMOTE-CONTROLLED WORK ROBOT

(75) Inventors: Hiroshi Isobe, Iwata (JP); Takayoshi Ozaki, Iwata (JP)

(73) Assignee: NTN Corporation, Osaka (JP)

(*) Notice: Subject to any disclaimer, the term of this patent is extended or adjusted under 35 U.S.C. 154(b) by 0 days.

(21) Appl. No.: 13/317,844

(22) Filed: Oct. 31, 2011

(65) Prior Publication Data

US 2012/0043100 A1 Feb. 23, 2012

Related U.S. Application Data

(63) Continuation of application No. PCT/JP2010/057545, filed on Apr. 28, 2010.

(30) Foreign Application Priority Data

May 8, 2009 (JP) ................................. 2009-113269

(51) Int. Cl.
   *B25J 17/02* (2006.01)
(52) U.S. Cl. .............. 173/190; 173/2; 173/44; 606/139; 606/180; 128/898; 901/8
(58) Field of Classification Search .................. 173/190, 173/44, 39, 2; 606/1, 139, 130, 180, 80, 606/85; 128/898, 922; 600/425, 427; 901/8
   See application file for complete search history.

(56) References Cited

U.S. PATENT DOCUMENTS

| | | | |
|---|---|---|---|
| 4,265,231 A | | 5/1981 | Scheller, Jr. et al. |
| 4,466,429 A | | 8/1984 | Loscher et al. |
| 5,762,458 A | * | 6/1998 | Wang et al. ........................ 414/1 |
| 5,769,092 A | | 6/1998 | Williamson, Jr. |
| 5,776,136 A | * | 7/1998 | Sahay et al. ..................... 606/79 |
| 6,007,550 A | * | 12/1999 | Wang et al. ..................... 606/139 |
| 6,063,095 A | * | 5/2000 | Wang et al. ..................... 606/139 |
| 7,125,403 B2 | * | 10/2006 | Julian et al. ........................ 606/1 |
| 7,223,274 B2 | * | 5/2007 | Vargas et al. .................. 606/153 |
| 7,373,219 B2 | * | 5/2008 | Nowlin et al. ................. 700/245 |
| 7,594,912 B2 | * | 9/2009 | Cooper et al. .................... 606/1 |

(Continued)

FOREIGN PATENT DOCUMENTS

DE 10 2006 030 688 A1 5/2000

(Continued)

OTHER PUBLICATIONS

International Search Report for PCT/JP2010/057545 mailed Aug. 3, 2010.

(Continued)

*Primary Examiner* — Scott A. Smith
(74) *Attorney, Agent, or Firm* — Staas & Halsey LLP

(57) ABSTRACT

A remote controlled work robot including a remote controlled actuator and a support device therefor. The remote controlled actuator includes a spindle guide section of an elongated configuration, a distal end member fitted to a distal end of the spindle guide section through a distal end member coupling structure for alteration in attitude, and a drive unit housing connected with a base end of the spindle guide section. The distal end member rotatably supports a spindle for holding a tool. The support device includes a single degree-of-freedom system, in which the remote controlled actuator has a degree of freedom in one direction, or a multi-degrees-of-freedom system, in which the remote controlled actuator has a two or more degrees of freedom relative to a base on which the support device is installed. A drive source and is also provided for driving the degree-of-freedom system.

12 Claims, 25 Drawing Sheets

U.S. PATENT DOCUMENTS 7,682,357 B2 * 3/2010 Ghodoussi et al. ............... 606/1
2007/0265653 A1 11/2007 Suzuki

FOREIGN PATENT DOCUMENTS

| JP | 60-25223 | 7/1985 |
|---|---|---|
| JP | 2-500568 | 3/1990 |
| JP | 2000-505328 | 5/2000 |
| JP | 2000-505665 | 5/2000 |
| JP | 2001-017446 | 1/2001 |
| JP | 2003-148999 | 5/2003 |
| JP | 2005-305585 | 11/2005 |
| JP | 2006-500998 | 1/2006 |
| JP | 2007-521916 | 8/2007 |
| JP | 2007-301149 | 11/2007 |
| WO | WO 88/02243 A1 | 4/1988 |
| WO | WO 97/29690 A1 | 8/1997 |
| WO | WO 97/31577 A1 | 9/1997 |
| WO | WO 2004/028351 A2 | 4/2004 |
| WO | WO 2005/077284 | 8/2005 |

OTHER PUBLICATIONS

International Preliminary Report on Patentability mailed Dec. 22, 2011 issued in corresponding International Patent Application No. PCT/JP2010/057545.

* cited by examiner

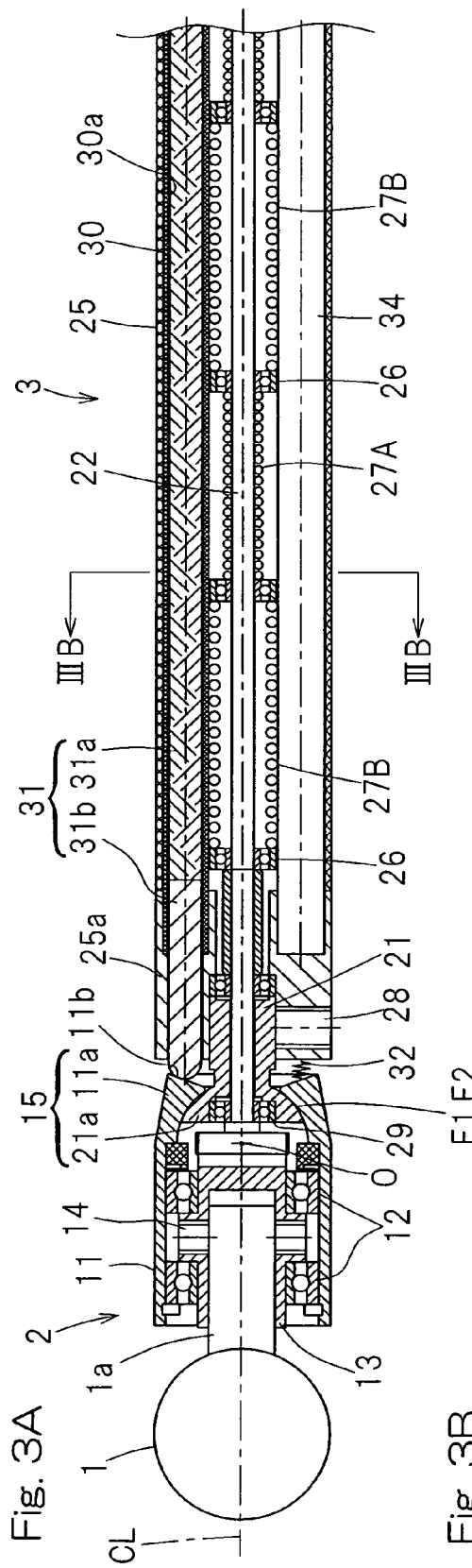
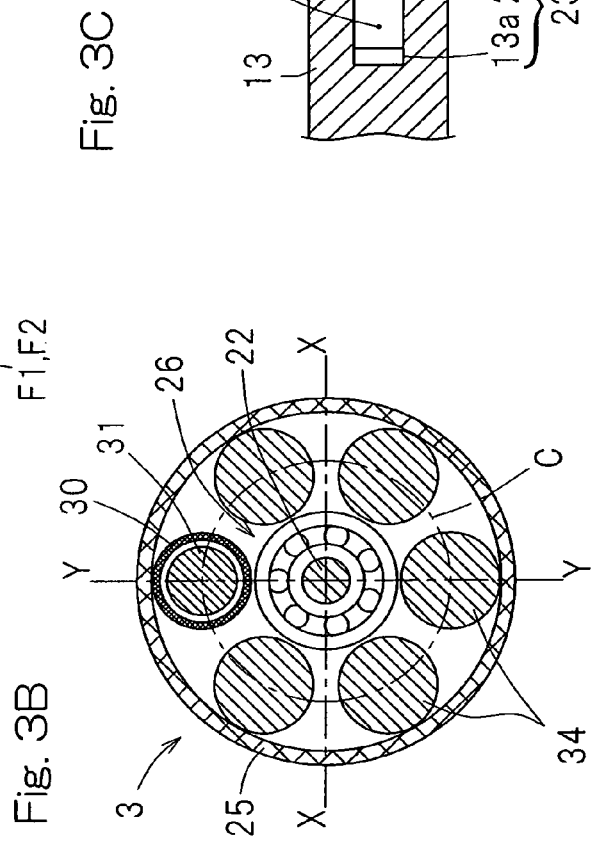
Fig. 3A
Fig. 3B
Fig. 3C

Fig. 7
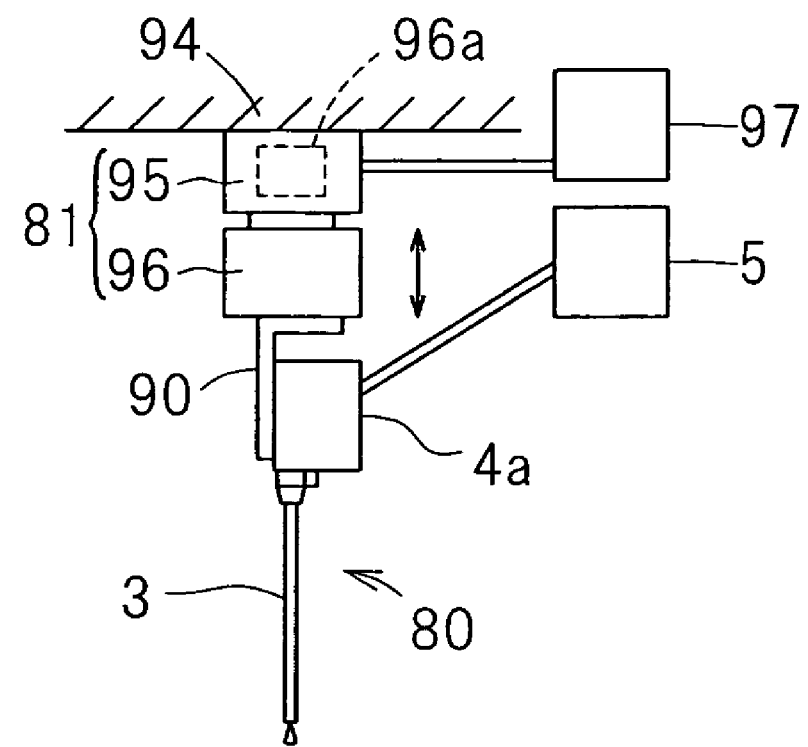
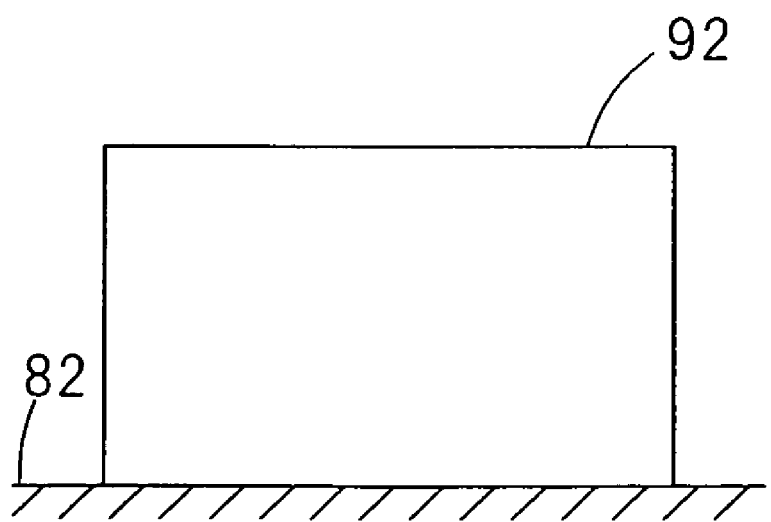

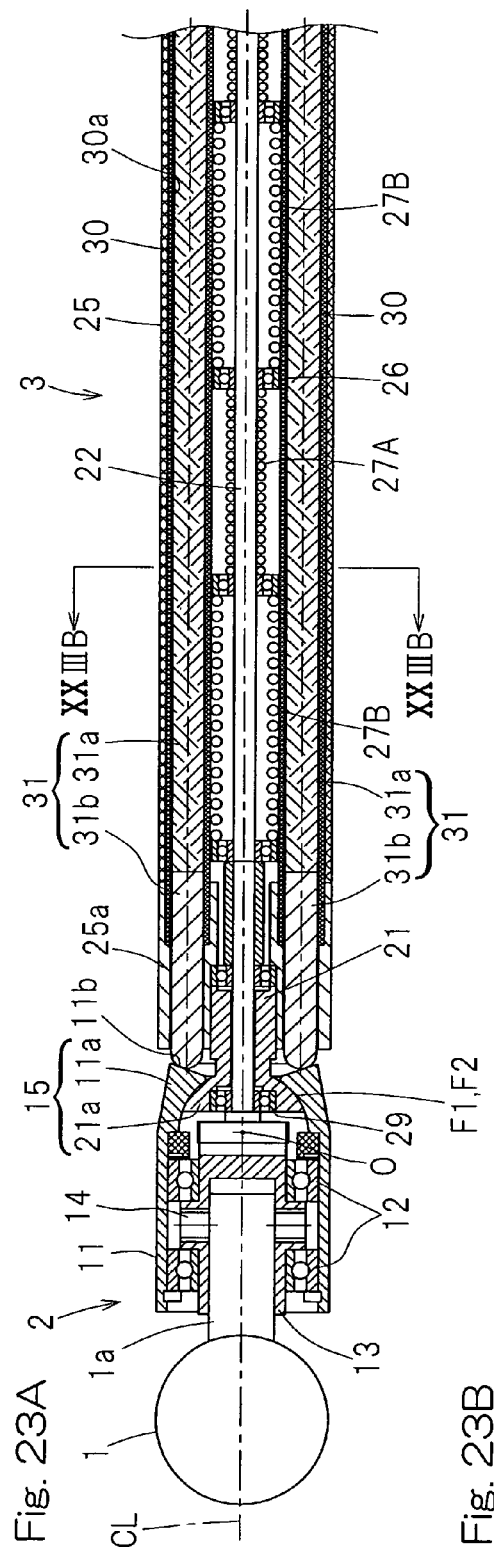
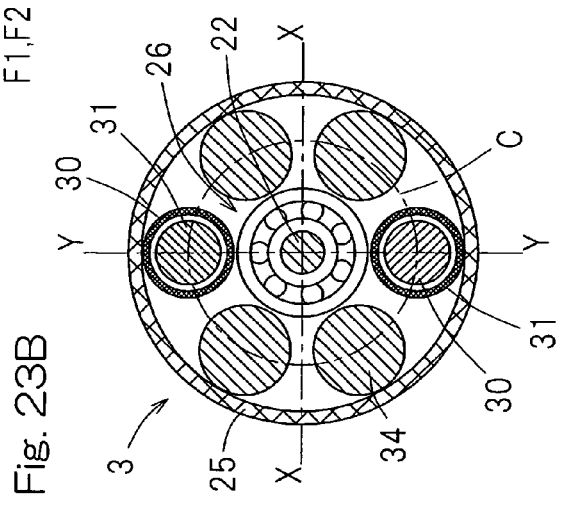
Fig. 23A
Fig. 23B

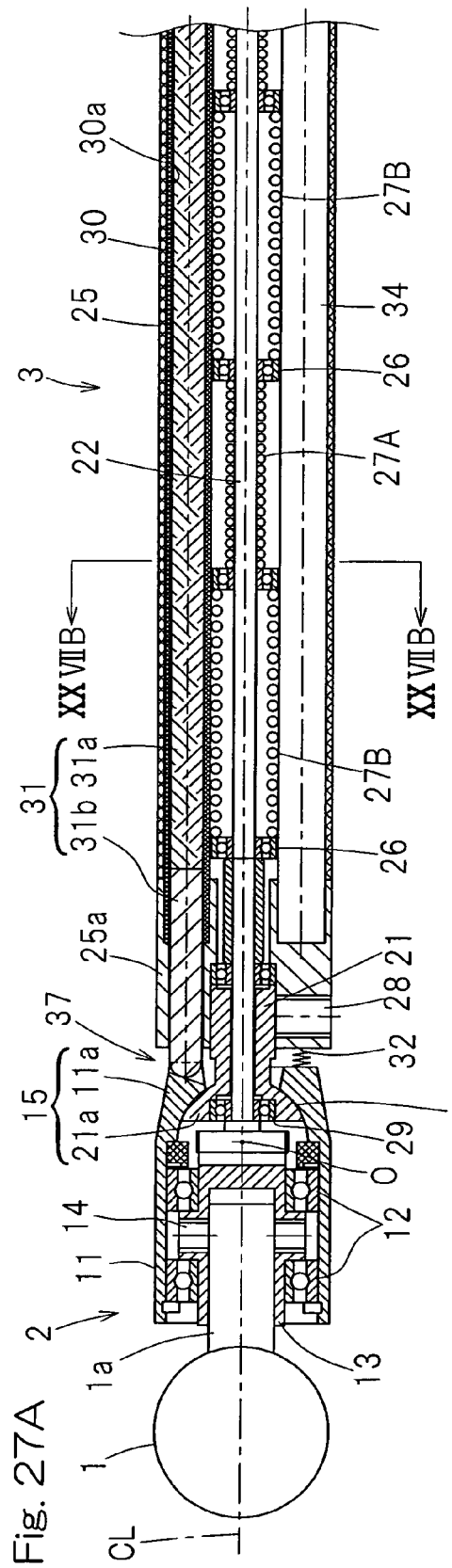
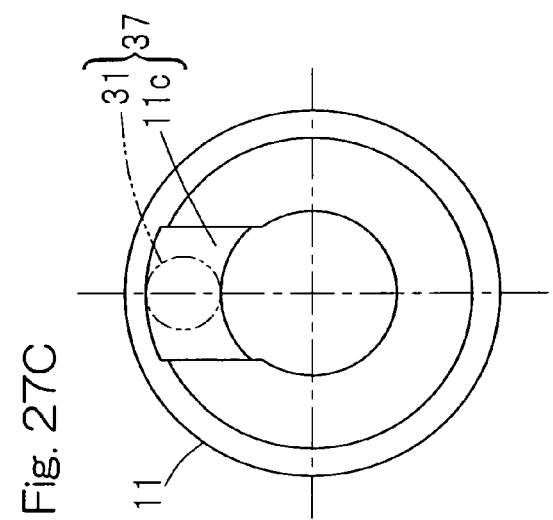
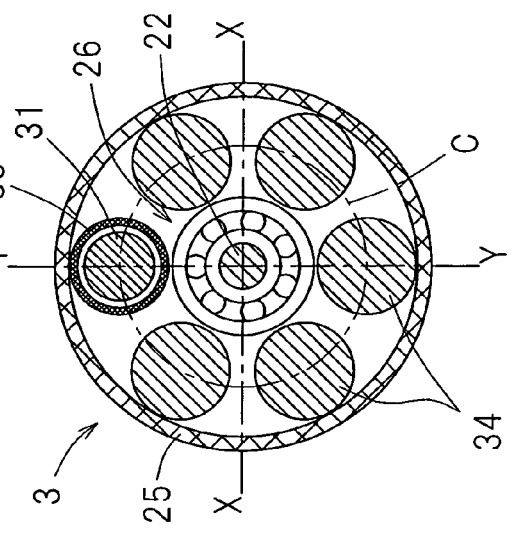

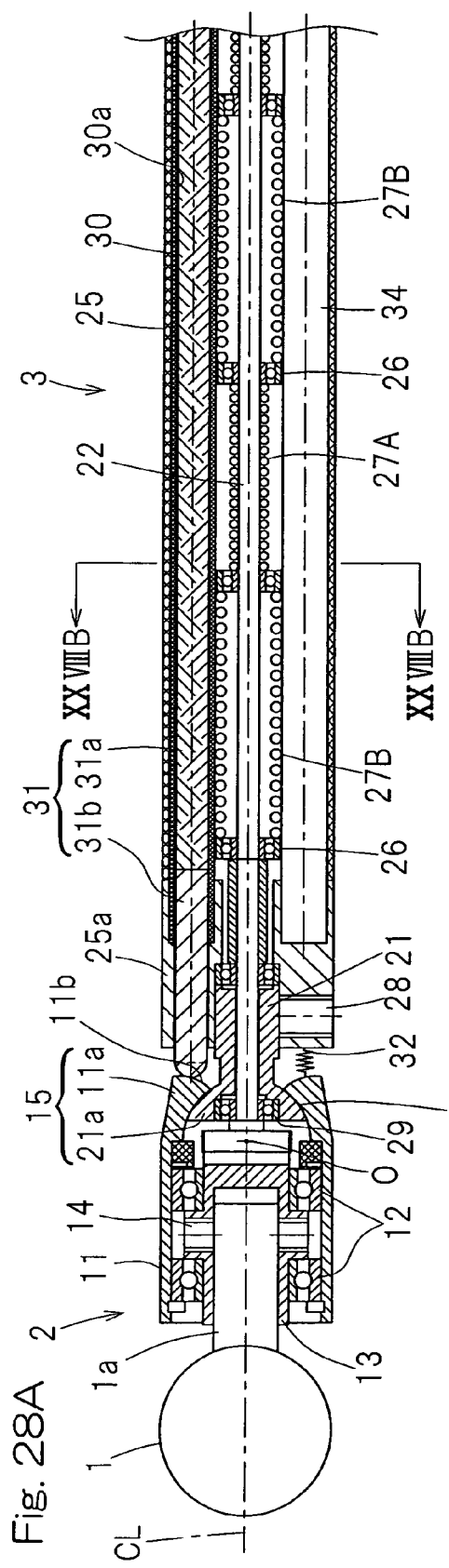
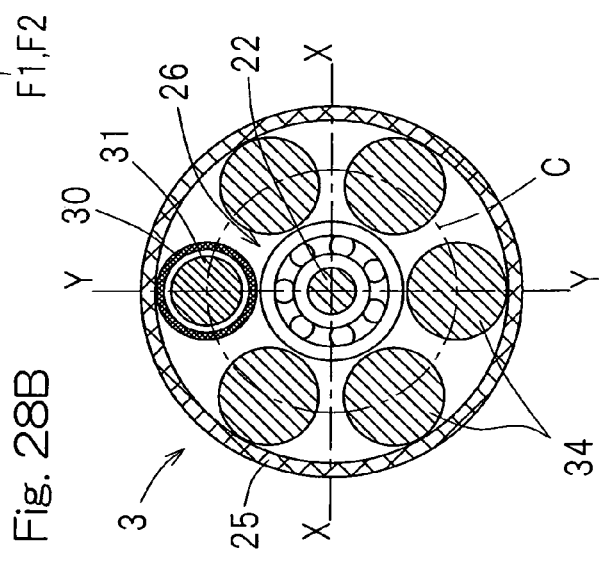
Fig. 28A
Fig. 28B

REMOTE-CONTROLLED WORK ROBOT

CROSS REFERENCE TO THE RELATED APPLICATION

This application is a continuation application, under 35 U.S. §111(a) of international application No. PCT/JP2010/057545, filed Apr. 28, 2010, which claims priority to a Japanese patent application No. 2009-113269, filed May 8, 2009, the entire disclosure of which is herein incorporated by reference as a part of this application.

BACKGROUND OF THE INVENTION 1. (Field of the Invention)

The present invention relates to a remote controlled actuator capable of altering the attitude of a tool by remote control and a support device therefor and, more particularly, to a remote controlled work robot for use in the application such as, for example, medical or mechanical processing.

2. Description of Related Art

Remote controlled actuators are currently known; some are used in the medical field for osteal treatment and some are used in the mechanical processing field for drilling and cutting. Any of those remote controlled actuators is of a design used to control by remote control a tool fitted to a distal end of an elongated pipe of a linear or curved configuration. In the medical field, however, since the conventional remote controlled actuator is designed to control only the rotation of the tool by remote control, difficulties have been encountered in dealing with a complicated shape and processing at a site difficult to view with eyes from the outside. Also, in the drilling procedure, the capability of dealing with not only the linear line, but also the curved configuration is often required. Furthermore, in the cutting procedure, the capability is required to perform the procedure at a site deep in a groove. In the following description, reference will be made to the medical field in discussing over the conventional art and problems inherent in the conventional remote controlled actuator.

In the orthopedic field, the artificial joint replacement is well known, in which a joint, of which bone has been abraded by reason of bone deterioration, is replaced with an artificial joint. The joint replacement surgery requires a living bone of a patient to be processed so that an artificial joint can be implanted. In order to increase the strength of postoperative adhesion between the living bone and the artificial joint, such procedure has to be performed precisely and accurately to suit to the shape of the artificial joint.

For example, during the hip join replacement surgery, an access opening for the insertion of an artificial joint therethrough into the femoral marrow cavity is formed in the thigh bone of a patient. In order to secure the strength of contact between the artificial joint and the bone, surfaces of contact of the artificial joint and the bore must be large and the access opening for insertion of the artificial joint has to be processed to represent an elongated shape extending deep into the bone. The medical actuator for use in bone cutting purpose has been known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

In the practice of the artificial joint replacement, skin incision and/or muscular scission are generally performed. In other words, the human body must be invaded physically. In order to minimize the postoperative trace, it is quite often desirable that the elongated pipe referred to above is not necessarily straight, but is moderately curved. To meet with this desire, the following technique has hitherto been suggested. For example, the Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated 180°.

[Prior Art Literature]

[Patent Document 1] JP Laid-open Patent Publication No. 2007-301149

[Patent Document 2] U.S. Pat. No. 4,466,429

[Patent Document 3] U.S. Pat. No. 4,265,231

[Patent Document 4] JP Laid-open Patent Publication No. 2001-17446

[Patent Document 5] U.S. Pat. No. 5,769,092

DISCLOSURE OF THE INVENTION

If in the condition with the artificial joint having been inserted into the artificial joint insertion opening formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion opening. Whatever the pipe take any shape, however, the working range of the tool is limited by the shape of the pipe and, therefore, difficulties have been encountered in processing the artificial joint insertion opening so that the living bone and the artificial joint may have smooth contact surfaces and, yet, skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion opening is more difficult to achieve than generally considered.

In view of the foregoing, the applicant or assignee of the present invention has attempted to provide a remote control actuator of a type designed to enable the processing of the artificial joint insertion opening to be relatively easily and accurately accomplished. For this purpose the remote controlled actuator of the type referred to above operates to alter an attitude of a tool by remote control. It has, however, been found that since the tool is connected to the distal end of the elongated pipe, disposition of a mechanism for changing the attitude of the tool is considerably limited and, therefore, artifices are required to overcome those limitations. This is because if the attitude of the tool can be changed, the tool can be maintained at a proper attitude regardless of the shape of the pipe. It is eventually pointed out that although the medical actuator of a type having no elongated pipe such as, for example, the spindle guide section, but in which a portion provided with a processing tool is changeable in attitude relative to the grip that is held by hand, is currently available in the medical field (See, for example, the Patent Document 4 listed below.), but nothing has yet been suggested which has a capability of changing the attitude of the tool by remote control.

Where one operates the remote controlled actuator while holding it by hand, wobbling, for example, of the hand holding the remote controlled actuator affects the accuracy of positioning of the tool relative to an object to be cut. For this reason, in order to accomplish the processing accurately, a substantial amount of experiences are needed. Particularly where the guide section is of a curved configuration, it is indeed difficult to predicate the position of the tool attached to the distal end of the guide section and the operation is further complicated and difficult to accomplish. This also results in an increase of the length of time required to finish the cutting. Where the remote controlled actuator is used in the artificial joint replacement surgery, the increased length of time required to accomplish the cutting tends to impose a substantial amount of load on the patient.

In view of the above, the remote controlled actuator is rendered to be a remote controlled work robot supported by a support device having one or two or more degrees of freedom. With such construction, undesirable influences brought about by the wobbling of the hand can be eliminated. This type of the remote controlled work robot is disclosed in, for example, the Patent Document 4 listed above, but since the conventional work robot is incapable of accomplishing a meticulous processing since the remote controlled actuator is of a type incapable of altering the attitude of the tool.

In view of the foregoing, the present invention is intended to provide a remote controlled work robot of a kind capable of supporting a remote controlled actuator at an accurate position and utilizing the remote controlled actuator of a type capable of altering the attitude of the tool, attached to the distal end of the elongated pipe section.

The remote controlled robot according to the present invention includes a remote controlled actuator and a support device for supporting the remote controlled actuator. The remote controlled actuator in turn includes a spindle guide section of an elongated configuration, a distal end member fitted to a distal end of the spindle guide section through a distal end member coupling structure for alteration in attitude and rotatably supporting a spindle for holding a tool, and a drive unit housing connected with a base end of the spindle guide section. The spindle guide section is of a structure in which a rotary shaft for transmitting a rotation of a tool rotation drive source, provided within the drive unit housing, to the spindle and an open ended guided hole are accommodated therein, an attitude altering member for altering the attitude of the distal end member when reciprocally moved with its distal end in engagement with the distal end member is reciprocally movably inserted within the guide hole, an attitude alteration drive source for reciprocally moving the attitude altering member is provided within the drive unit housing. On the other hand, the support device in turn includes a single degree-of-freedom system, in which the remote controlled actuator has a degree of freedom in one direction, or a multi-degrees-of-freedom system, in which the remote controlled actuator has a two or more degrees of freedom relative to a base on which the support device is installed, and a drive source for operating a movable part of the degree-of-freedom system.

According to the construction described above, since the remote controlled actuator is supported by the support device, the position and attitude of the remote controlled actuator can be stabilized. The support device is of a single degree-of-freedom system or a multi-degrees-of-freedom system, and when the movable part of the degree-of-freedom system is operated by the drive source, the position and attitude of the remote controlled actuator can be arbitrarily altered.

The remote controlled actuator performs a cutting of the bone through the rotation of the tool provided in the distal end member. At this time, when the attitude altering member is selectively advanced or retracted by the attitude alteration drive source, the attitude of the distal end member fitted to the distal end of the spindle guide section for alteration in attitude through the distal end member coupling structure can be altered as the distal end of the attitude altering member works on the distal end member. The attitude alteration drive source is provided within the drive unit housing on a base end side of the spindle guide section and the alteration of the attitude of the distal end member is carried out by remote control. Since the attitude altering member is inserted within the guide hole, there is no possibility of the attitude altering member displacing in position in a direction perpendicular to the longitudinal direction of the attitude altering member and can properly work on the distal end member at all times and the alteration in attitude of the distal end member can be performed accurately.

As hereinabove described, since the remote controlled actuator can be stably supported at any arbitrarily position in any arbitrarily attitude by the support device and, at the same time, the alternation in attitude of the tool of the remote controlled actuator can be performed accurately, a meticulous processing can be accomplished. More specifically, a processing in a narrow site or an accurate processing can be accomplished. Also, the length of time required to complete the processing can also be reduced. Accordingly, when the remote controlled work robot of the present invention is used for surgical purpose, the burden of the patient can be relieved.

In the present invention, it is preferred to provide the remote controlled work robot with a controller for controlling the remote controlled actuator and the support device by remote control.

When with the use of the controller for remotely controlling the remote controlled actuator and the support device the remote controlled work robot in its entirety is controlled by remote control, the processing can be performed according to a navigation that suit to a preset program or situation and, therefore, a further meticulous processing can be accomplished.

In the present invention, where the support device includes the multi-degrees-of-freedom system, the multi-degrees-of-freedom system may be of a structure including three or more sets of a link mechanisms, in each of which an end link member is connected for rotation relative to an input member, arranged on an input side, and an output member, arranged on an output side, and respective end link members on the input and output sides are connected for rotation relative to an intermediate link member; with respect to a transverse section at a center portion of each of the link mechanisms, the input side and the output side are geometrically identical with each other; of turning pair or revolute pair of each of the link mechanism connected with the input member, with respect to two or more sets of the link mechanisms a link mechanism drive source for controlling arbitrarily the attitude of the output member is provided as the drive source. In other words, the input and output sides of each of the link mechanism are identical in link shape and dimension with each other.

In such case, the support device is such that the input member of the multi-degrees-of-freedom system is connected with the base and the output member is connected with the drive unit housing for the remote controlled actuator.

Alternatively, the support device may be such that the input member of the multi-degrees-of-freedom system thereof is connected with the base and the output member is provided with a translatory mechanism form translationally moving the movable part relative to a stationary part fixed to the output member, the movable part of the translatory mechanism being connected with the drive unit housing for the remote controlled actuator.

According to the foregoing construction of the multi-degrees-of-freedom system, the wide operating range of the output member can be available. By way of example, the maximum bending angle delimited between the center axis of the input member and the center axis of the output member is about ±90°, and the angle of swivel of the output member relative to the input member can be set to a value within the range of 0 to 360°. Since with respect to the two or more sets of the link mechanisms among the turning pair of each of the link mechanisms connected with the input member, a link mechanism drive source for controlling arbitrarily the attitude of the output member is provided, the output member can be easily set to any arbitrary attitude. That the turning pair of the link mechanism, where the link mechanism drive source is provided, is chosen to be the two or more sets is necessitated to ensure the attitude of the output member relative to the input member.

When the input member is connected with the base and the output member is connected with the drive unit housing for the remote controlled actuator, the attitude of the remote controlled actuator relative to the base can be determined.

Also, if the output member is provided with the translatory mechanism and the movable part of this translatory mechanism is connected with the drive unit housing for the remote controlled actuator, not only can the attitude of the remote controlled actuator relative to the base be determined as desired, but the position of the remote controlled actuator relative to the base can also be determined as desired. For this reason, the operating range of the output member is further expanded and the degree of freedom of the processing with the remote controlled actuator can be increased.

It is preferred that a wiring for electrically connecting between the remote controlled actuator or the translatory mechanism and the controller be passed within the three or more sets of the link mechanisms.

To pass the wiring within the three or more sets of the link mechanisms is effective to facilitate the wiring and the wiring will no longer constitute any obstruction.

Where a bearing is employed for rotatably supporting the rotary shaft within the spindle guide section, the use is preferred of a cooling section for cooling the bearing with a cooling liquid then flowing through the spindle guide section.

The spindle for rotating the tool and some rotatable members such as, for example, the rotary shaft tend to evolve heat as a result of rotational friction. This in turn results in heat evolution in the bearing. The use of the bearing cooling section referred to above is effective to cool the heat evolving site of the bearing with the cooling liquid. If the cooling liquid is allowed to flow within the spindle guide section, there is no need to employ any extra tube for the supply and flow of the cooling liquid and, hence, the spindle guide can be simplified and downsized in diameter.

Furthermore, an effect of lubricating the bearing with the cooling liquid can be obtained. If the cooling liquid is concurrently used for lubrication of the bearing, there is no need to use a grease which is generally employed in bearings, and, moreover, no extra lubricating device is needed.

The use may be made of a tool cooling device for cooling the tool with a cooling liquid then supplied from the outside or with a cooling liquid then flowing through the spindle guide section.

During the processing, the tool and the to-be-processed object evolve heat. However, the use of the tool cooling device is effective to allow the tool and the to-be-processed object to be cooled with the cooling liquid.

The cooling liquid is preferably employed in the form of water or physiological saline.

If the cooling liquid is employed in the form of water or physiological saline, the cooling liquid will bring no adverse effect on the living body particularly where the processing is performed with the distal end member inserted into the living body.

In the present invention, the spindle guide section may have a portion thereof curved.

Since the operating member is flexible, it can be selectively advanced or retracted within the guide bole even in the presence of that curved portion in the spindle guide section.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 3A is a sectional view of a distal end member and a spindle guide section both forming respective parts of the remote controlled actuator;

FIG. 3B is a cross sectional view taken along the line IIIB-IIIB in FIG. 3A;

FIG. 3C is a diagram showing a coupling structure between the distal end member and a rotary shaft;

FIG. 7 is a diagram showing a schematic structure of the remote controlled work robot according to a third preferred embodiment of the present invention;

FIG. 23A is a sectional view showing the distal end member and the spindle guide section, both employed in the remote controlled actuator according to a fourteenth preferred embodiment of the present invention;

FIG. 23B is a cross sectional view taken along the line XXIIIB-XXIIIB in FIG. 23A;

FIG. 27A is a sectional view showing the distal end member and the spindle guide section, both employed in the remote controlled actuator according to a seventeenth preferred embodiment of the present invention;

FIG. 27B is a cross sectional view taken along the line XXVIIB-XXVIIB in FIG. 27A;

FIG. 27C is a view showing a housing for the distal end member as viewed from a base end side;

FIG. 28A is a sectional view showing the distal end member and the spindle guide section, both employed in the remote controlled actuator according to an eighteenth preferred embodiment of the present invention; and FIG. 28B is a cross sectional view taken along the line XXVIIIB-XXVIIIB in FIG. 28A.

DESCRIPTION OF PREFERRED EMBODIMENTS

Figure 1:
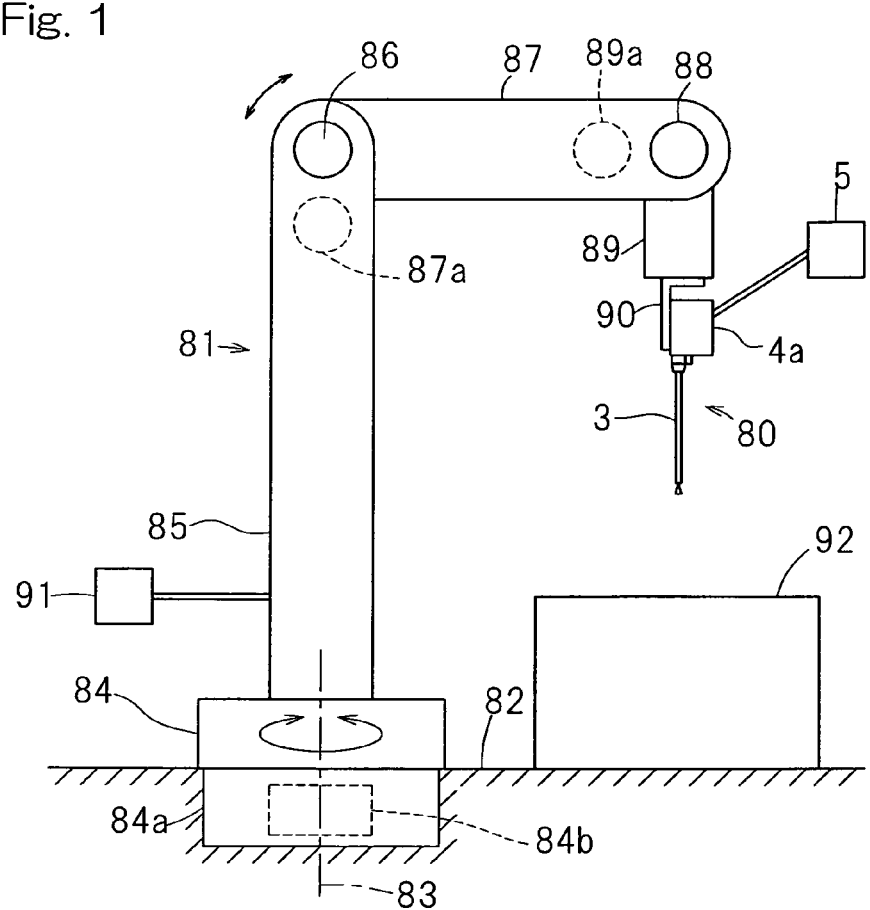
FIG. 1 is a diagram showing a schematic structure of a remote controlled work robot according to a first preferred embodiment of the present invention.

A first preferred embodiment of the present invention will be described in detail with particular reference to FIGS. 1 to 4. As best shown in FIG. 1, a remote controlled work robot includes a remote controlled actuator 80 and a support device 81 for supporting the remote controlled actuator 80. In the illustrated embodiment, the support device 81 includes a rotatable platform 84 rotatable about a vertical axis 83 relative to a floor surface 82, which provides a base on which the support device 81 is installed, a stationary link 85 fixed to the rotatable platform 84, a pivot link 87 connected with an upper end of the stationary link 85 for pivotal movement about a pivot shaft 86, and a pivot arm 89 connected pivotally with a free end of the pivot link 87 by means of a pivot shaft 88, and the remote controlled actuator 80 is supported by the pivot arm 89 through a mounting stand 90. In other words, the support device 81 has an axis of rotation of the rotatable platform 84, a first movable articulate joint defined between the stationary link 85 and the pivot link 87 and a second movable articulate joint defined between the pivot link 87 and the pivot arm 89 and is hence rendered to be of a three-degrees-of-freedom system having three degrees of freedom.

More specifically, the rotatable platform 84 referred to above is rotatably supported by a pedestal 84a embedded below the floor surface 82, and the rotatable platform 84, which is a member movable relative to the pedestal 84a, is driven by a rotation drive source 84b. The first articulate joint is such that the pivot link 87, which is a member movable relative to the stationary link 85, is pivoted by a rotation drive source 87a. The second articulate is such that the pivot arm 89, which is a member movable relative to the pivot link 87, is pivoted by a rotation drive source 89a. Those drive sources 84b, 87a and 89a are controlled by a support device controller 91 for a three-degrees-of-freedom system forming a part of the support device 81. The controller 91 for the three-degree-of-freedom system includes electronic circuits and operating switches. The electronic circuits include a computer such as, for example, a microcomputer. Support device controller 97, 98 and an actuator controller 5, both of which are described later, have a structure similar to the controller 91 for the three-degrees-of-freedom system.

Figure 2:
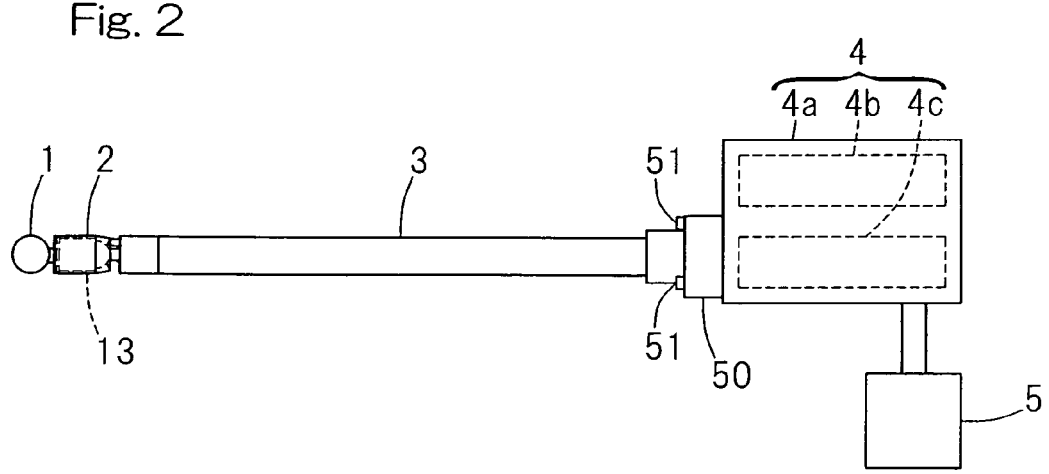
FIG. 2 is a diagram showing a schematic structure of a remote controlled actuator used in the remote controlled work robot.

As shown in FIG. 2, the remote controlled actuator 80 includes a distal end member 2 for holding a rotary tool 1, an elongated spindle guide section 3 fitted to a distal end of the distal end member 2 for alteration in attitude, a drive unit hosing 4a to which a base or proximal end of the spindle guide section 3 is connected, and the actuator controller 5 for controlling a tool rotation drive mechanism 4b and an attitude alteration drive mechanism 4c, the both of which are accommodated within the drive unit housing 4a. The drive unit housing 4a cooperates with the built-in tool rotation drive mechanism 4b and the similarly built-in attitude alteration drive mechanism 4c to define a drive unit 4. The mounting stand 90 referred to previously is secured to the drive unit housing 4a.

Referring particularly to FIG. 3A illustrating a sectional representation of the distal end member 2 and the spindle guide section 3, which form respective parts of the remote controlled actuator 80. The distal end member 2 includes a spindle 13 rotatably supported within a generally cylindrical housing 11 by means of a pair of bearings 12. The spindle 13 is of a hollow cylindrical configuration having a distal end open and a base or proximal end closed, and a shank 1a of the tool 1 is snugly inserted into the hollow thereof and is rotatably immovably connected therewith by means of a stopper pin 14. This distal end member 2 is fitted to a distal end of the spindle guide section 3 through a distal end member coupling structure 15. The distal end member coupling structure 15 is a section for supporting the distal end member 2 for alteration in attitude thereof and is in the form of a spherical bearing. More specifically, the distal end member coupling structure 15 is made up of a to-be-guided member 11a, which is comprised of a reduced inner diameter portion of a base end of the housing 11, and a guide member 21a which is comprised of a collar portion of a detent member 21 fixed in the distal end of the spindle guide section 3. Respective guide surfaces F1 and F2 of those members 11a and 21a, which are held in contact with each other, have respective centers of curvature O positioned on a longitudinal center line CL of the spindle 13 and are rendered to be a spherical surface having a diameter smaller on a base end side. Accordingly, the distal end member 2 is locked in position relative to the spindle guide section 3 and is also supported for alteration in attitude relative to the spindle guide section 3.

Figure 4A:
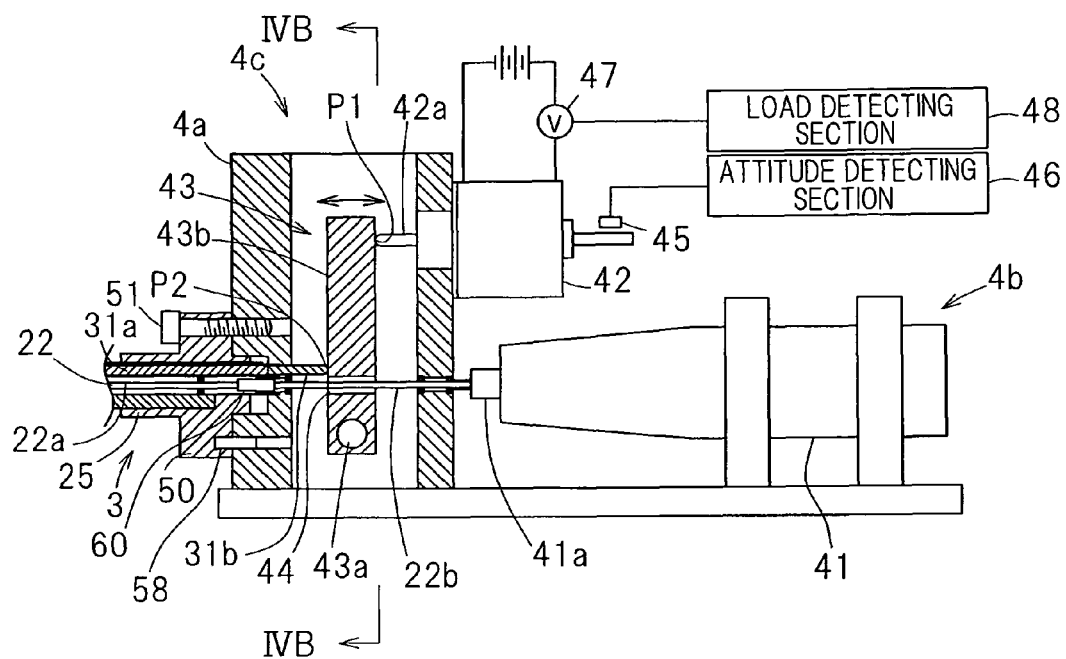
FIG. 4A is a sectional view showing a tool rotation drive mechanism and an attitude alteration drive mechanism both used in the remote controlled actuator.
Figure 4B:
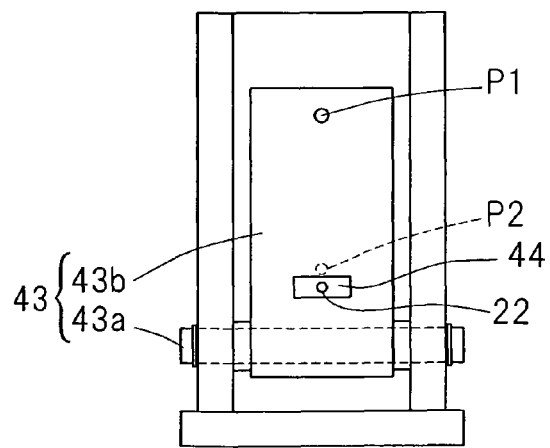
FIG. 4B is a cross sectional view taken along the line IVB-IVB in FIG. 4A.

The spindle guide section 3 has a rotary shaft 22 accommodated therein for transmitting a rotational force of the tool rotation drive source 41 within the drive unit housing 4a, shown in FIGS. 4A and 4B, to the spindle 13. In the illustrated embodiment, the rotary shaft 22 is employed in the form of a wire and is, hence, made elastically deformable to a certain extent. Material for the wire may be employed in the form of, for example, metal, resin or glass fibers. The wire may be a single wire or a twisted wire.

As best shown in FIG. 3C, the spindle 13 and the rotary shaft 22 are connected with each other through a coupling 23 such as, for example, a universal joint for transmission of rotational force from the rotary shaft 22 to the spindle 13, and vice versa. The coupling 23 referred to above is comprised of a groove 13a, defined in a closed base end of the spindle 13, and an engagement 22a engageable in the groove 13a provided in the distal end of the rotary shaft 22. The center of connection between the groove 13a and the engagement 22a lies at the same position as the centers of curvature O of the guide surfaces F1 and F2. It is to be noted that the rotary shaft 22 and the engagement 22a may be respective members separate from each other.

The spindle guide section 3 includes an outer shell pipe 25 defining an outer shell for the spindle guide section 3, and the rotary shaft 22 referred to previously is positioned at the center of this outer shell pipe 25. The rotary shaft 22 is rotatably supported by a plurality of rolling bearings 26 arranged having been spaced a distance from each other in an axial direction of the spindle guide section 3. Spring elements 27A and 27B for generating respective preloads to those rolling bearings 26 are interposed between the neighboring members of those rolling bearings 26. The spring elements 27A and 27B are employed in the form of, for example, compression coil springs, respectively. Those spring elements includes an inner ring spring element 27A for generating a preload to an inner ring of each of the rolling bearings 26 and an outer ring spring element 27B for generating a preload to an outer ring thereof, and those spring elements 27A and 27B are arranged alternately. The detent member 21 referred to previously is fixed to a pipe end portion 25a by means of a fixing pin 28 and rotatably supports a distal end portion of the rotary shaft 22 at its distal end inner portion through a rolling bearing 29. It is, however, to be noted that the pipe end portion 25a may be a member separate from the outer shell pipe 25 and, in such case, it may be connected with the outer shell pipe 25 by means of, for example, welding.

An open-ended single guide pipe 30 having its opposite ends open is provided between an inner diametric surface of the outer shell pipe 25 and the rotary shaft 22, and an attitude altering member 31 comprised of a wire 31a and pillar shaped pins 31b at opposite ends of the wire 31a is inserted in a guide hole 30a, which is an inner diametric hole of the guide pipe 30, for selective advance and retraction. One end of the pillar shaped pin 31b on the side adjacent the distal end member 2 is spherical in shape and is held in contact with a base end face of the housing 11 for the distal end member 2, which base end face is a surface of contact with the attitude altering member 31. The base end face 11b of the housing 11 is rendered to be an inclined face with its outer diametric side closer to the side of the spindle guide section 3. One end of the pillar shaped pin 31b on the side adjacent the drive unit housing 4a is also spherical in shape and is held in contact with a side face (a distal end side face) of a lever 43b as shown in FIG. 4A and as will be described later. It is, however, to be noted that the use of the pillar shaped pins 31b may be dispensed with to allow the attitude altering member 31 to be comprised solely of the single wire 31a.

At a position spaced 180° in phase relative to a circumferential position, where the attitude altering member 31 is positioned, a elastic restoring member 32 in the form of, for example, a compression coil spring, is provided between the base end face of the housing 11 for the distal end member 2 and a distal end face of the outer shell pipe 25 of the spindle guide section 3. This elastic restoring member 32 functions to bias the distal end member 2 in a direction required to permit it to assume a predetermined attitude.

Also, separate from the guide pipe 30 referred to previously, a plurality of reinforcement shafts 34 are provided between the inner diametric surface of the outer shell pipe 25 and the rotary shaft 22 and arranged on the same pitch circle C as that of the guide pipe 30. Those reinforcement shafts 34 are employed to secure the rigidity of the spindle guide section 3. The guide pipe 30 and the reinforcement shafts 34 are circumferentially equidistantly arranged. The guide pipe 30 and the reinforcement shafts 34 are held in contact with the inner diametric surface of the outer shell pipe 25 and respective outer diametric surfaces of the rolling bearings 26. Accordingly, the outer surfaces of those rolling bearings 26 are supported thereby.

FIG. 4A illustrates the tool rotation drive mechanism 4b and the attitude alteration drive mechanism 4c both accommodated within the drive unit housing 4a. The tool rotation drive mechanism 4b includes a tool rotation drive source 41. The tool rotation drive source 41 is, for example, an electric drive motor and has its output shaft 41a coupled with the base end of the rotary shaft 22. It is to be noted that the rotary shaft 22 is passed through an opening 44, which is a throughhole defined in the lever 43b as will be described later.

The attitude alteration drive mechanism 4c includes an attitude alteration drive source 42 associated with the altitude altering member 31. This attitude alteration drive source 42 is in the form of, for example, an electrically operated linear actuator and movement of an output rod 42a movable in a leftward and rightward direction as viewed in FIG. 4A is transmitted to the attitude altering member 31 through a force increasing and transmitting mechanism 43. The force increasing and transmitting mechanism 43 includes the pivotable lever 43b pivotable about a support pin 43a in a direction leftwards or rightwards as indicated by the arrows in FIG. 4A, and is so designed and so configured that a force of the output rod 42a can act on a working point P1 of the lever 43b, which is spaced a long distance from the support pin 43a and a force is applied to the attitude altering member 31 at a working point P2 which is spaced a short distance from the support pin 43a, and an output of the attitude alteration drive source 42 is, after having been increased, transmitted to the attitude altering member 31. Since the use of the force increasing and transmitting mechanism 43 is effective to permit even the linear actuator of a small output to apply a large force to the attitude altering member 31, the linear actuator can be downsized. The attitude alteration drive source 42 may be in the form of, for example, a rotary motor. Also, instead of the use of the linear actuator, the attitude of the distal end member 2 may be manually operated by remote control.

The attitude alteration drive mechanism 4c is provided with an actuating amount detector 45 for individually detecting the actuating amount of each of the attitude alteration drive sources 42. A detection value of this actuating amount detector 45 is outputted to an attitude detecting section 46. The attitude detecting section 46 detects a tilted attitude of the distal end member 2 about an X-axis shown in FIG. 3B in dependence on the output of the actuating amount detector 45. The attitude detecting section 46 includes a relation setting section (not shown), in which relations between the inclined attitude and the output signal of the actuating amount detector 45 are set in terms of calculation equations and/or tables, and detects the inclined attitude in reference to the inputted output signal with the use of the relation setting section (not shown). This attitude detecting section 46 may be provided in the actuator controller 5 or, alternatively, in an external control device.

Also, the attitude alteration drive mechanism 4c is provided with a supplied power meter 47 for individually detecting the amount of an electric power supplied to the attitude alteration drive source 42, which is the electrically operated actuator. A detection value of this supplied power meter 47 is outputted to a load detecting section 48. The load detecting section 48 in turn detects a load, acting on the distal end member 2, in reference to an output of the supplied power meter 47. The load detecting section 48 includes a relation setting section (not shown), in which relations between the load and the output signal of the supplied power meter 47 are set in terms of calculation equation and/or tables, and detects the load with the use of this relation setting section in reference to the inputted output signal. This load detecting section 48 may be provided in the actuator controller 5 or, alternatively, in the external control device.

The actuator controller 5 referred to above controls the tool rotation drive source 41 and the attitude alteration drive source 42 based on the respective detection values of the attitude detecting section 46 and the load detecting section 48.

In the embodiment now under discussion, the spindle guide section 3 and the drive unit housing 4a are coupled together in the manner which will now be described. Specifically, the base end of the spindle guide section is formed integrally with a flange 50, and this flange 50 is bolted to the drive unit housing 4a by means of a plurality of set bolts 51. By a phase matching pin 58, respective phases of the flange 50 and the drive unit housing 4a about an axis of the rotary shaft 22 are matched with each other. Also, the rotary shaft 22 is comprised of an intro-guide shaft portion 22a, accommodated within the spindle guide section 3, and an intro-housing shaft portion 22b accommodated within the drive unit housing 4a, and the intro-guide shaft portion 22a and the intro-housing shaft portion 22b are connected with each other by means of a coupling 60 for rotation together with each other and, also axial movement relative to each other so that not only can they rotate together, but also they can be axially separated from each other. It is to be noted that in the embodiment now under discussion, the flange 50 has been shown and described as a member separate from the outer shell pipe 25 of the spindle guide section 3, it may be formed integrally with the outer shell pipe 25 if so desired.

The operation of the remote controlled actuator 80 of the structure hereinabove described will now be described. When the tool rotation drive source 41 is driven, the rotational force thereof is transmitted to the spindle 13 through the rotary shaft 22 to drive the tool 1 together with the spindle 13. The load acting on the distal end member 2 during the bone cutting taking place with the tool 1 so driven is detected by the load detecting section 48 in reference to the detection value of the supplied power meter 47. When the feed amount of the remote controlled actuator 80 in its entirety and the attitude alteration of the distal end member 2, as will be described, are controlled in dependence on the value of the load so detected, the bone can be cut under the condition in which the load acting on the distal end member 2 is maintained properly.

During the use, the attitude alteration drive source 42 is driven and the attitude alteration of the distal end member 2 is effected by remote control. For example, when the attitude altering member 31 is advanced towards the distal end side by the attitude alteration drive source 42, the housing 11 for the distal end member 2 is urged by the attitude altering member 31, with the consequence that the attitude of the distal end member 2 is altered with the distal end side oriented downwardly along the guide faces F1 and F2 as shown in FIG. 3A. Conversely, when the attitude altering member 31 is retracted by the attitude alteration drive source 42, the housing 11 for the distal end member 2 is urged backwards by an elastic repulsive force of the elastic restoring member 32, with the consequence that the attitude of the distal end member 2 is altered with the distal end side oriented upwardly along the guide faces F1 and F2. At this time, a pressure of the attitude altering member 31, the elastic repulsive force of the elastic restoring member 32 and a reactive force from the detent member 21 act on the distal end member coupling structure 15 and, accordingly, the attitude of the distal end member 2 is determined by the balance of those working forces. The attitude of the distal end member 2 is detected by the attitude detecting section 46 from the detection value of the actuating amount detector 45. For this reason, the attitude of the distal end member can be properly controlled by remote control.

The housing 11 for the distal end member 2 has a base or distal end face 11b inclined so as to approach the spindle guide section 3 as it goes towards an outer diametric side and, accordingly, when the attitude altering member 31 presses the base end face 11b of the housing 11, the base end face 11b of the housing 11 is apt to undergo a slippage relative to the attitude altering member 31, allowing the attitude of the housing 11 to be smoothly altered.

Since the attitude altering member 31 is inserted in the guide hole 30a of the guide pipe 30, no displacement of the attitude altering member 31 in a direction perpendicular to the lengthwise direction thereof occurs and, therefore, it acts on the distal end member 2 properly, thus accomplishing the attitude altering operation of the distal end member 2. Also, since the attitude altering member 31 is in the form of the wire and is therefore flexible, the attitude altering operation of the distal end member 2 takes place assuredly even when the spindle guide 3 is in a condition being curved. Yet, since the center of the coupling structure between the spindle 13 and the rotary shaft 22 lies at the same position as the centers 0 of curvature of the guide faces F1 and F2, neither a pressing force nor a withdrawing force act on the rotary shaft 22 upon alteration in attitude of the distal end member 2 and the distal end member 2 can be smoothly altered in attitude.

The spindle guide section 3 being of the elongated configuration requires the rotary shaft 22 and the attitude altering member 31 to be provided in a protected fashion within the spindle guide section 3, and the rotary shaft 22 is provided at the center of the outer shell pipe 25 and the guide pipe 30, accommodating therein the attitude altering member 31. Furthermore, the reinforcement shafts 34 are juxtaposed in a direction circumferentially of the outer shell pipe 25 at a location between the outer shell pipe 25 and the rotary shaft 22. Accordingly, it is possible to protect the rotary shaft 22 and the attitude altering member 31 and also to render the interior to be hollow to thereby reduce the weight and to secure the rigidity. Also, the whole is in good balance.

Since the rolling bearings 26 for supporting the rotary shaft 22 have their outer diametric surfaces supported by the guide pipe 30 and the reinforcement shafts 34, the outer diametric surfaces of the rolling bearings 26 can be supported with no need to use any extra component parts. Also, since the preloads are applied to the rolling bearings 26 by the spring elements 27A and 27B, the rotary shaft 22 in the form of the wire can be driven at a high speed. For these reasons, the spindle 13 can be machined while being driven at a high speed, the processing finish is good and the cutting resistance acting on the tool 1 can be reduced. Since the spring elements 27A and 27B are provided between the neighboring rolling bearings 26, the spring elements 27A and 27B can be provided without increasing the diameter of the spindle guide section 3.

The remote controlled work robot of the present invention is of the type that is used in, for example, cutting the bone of a patient during the artificial joint replacement surgery to form the access opening for the insertion of an artificial joint and, at this occasion, the remote controlled actuator 80 is so installed as to occupy position above a surgical bed 92 so that the surgical operation can be performed on the patient then lying on the surgical bed 92. During the surgical operation, the processing of the patient's bone is carried out by, for example, inserting the distal end member 2 and the spindle guide section 3 of the remote controlled actuator 80 into the patient's body. If the attitude of the distal end member 2 were to be alterable in a manner described hereinbefore, the patient's bone can be processed in a condition, in which the tool 1 is maintained in a proper attitude at all times, and the access opening for the insertion of the artificial joint can be formed accurately.

Since the remote controlled actuator 80 is supported by the support device 81, the position and the attitude of the remote controlled actuator 80 are stabilized. Where the remote controlled actuator 80 is manipulated by, for example, a surgeon then holding the remote controlled actuator in hand, there is a high possibility that the positioning accuracy of the tool 1 will be lowered as a result of the hand wobbling. However, the remote controlled worm robot of the present invention is effective to eliminate such possibility. Since in the case of the illustrated embodiment the support device 81 has the three-degrees-of-freedom system, the position and the attitude of the remote controlled actuator 80 can be altered arbitrarily as desired and the meticulous processing can be performed. More specifically, the processing of a narrow site and an accurate processing can be performed. Also, the length of time required to accomplish the processing can be reduced. In any event, the load on the patient can be relieved.

Figure 5:
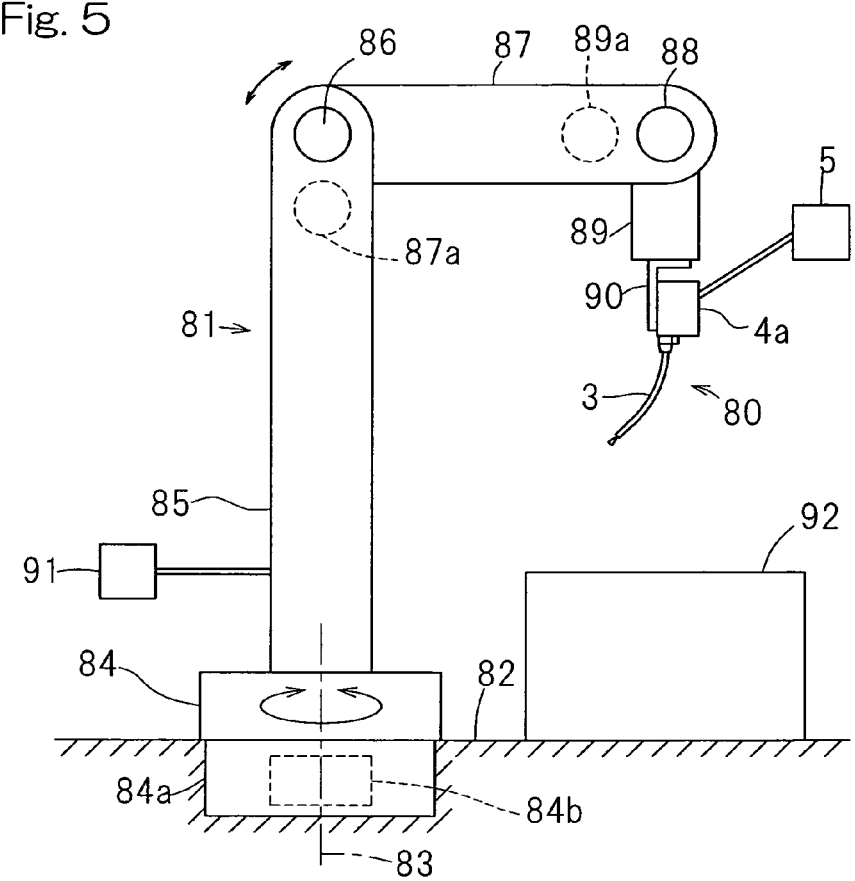
FIG. 5 is a diagram showing a schematic structure of the remote controlled work robot according to a second preferred embodiment of the present invention.
Figure 6:
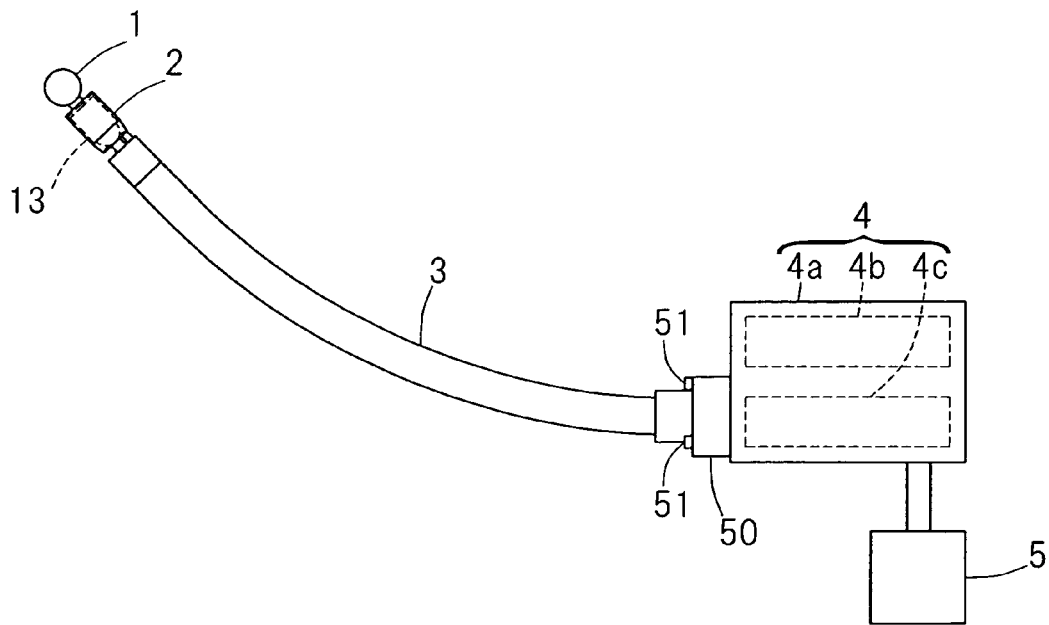
FIG. 6 is a diagram showing a schematic structure of the remote controlled actuator used in the remote controlled work robot.

As is the case with a second preferred embodiment of the present invention shown in FIGS. 5 and 6, for the remote controlled actuator 80, the type in which the spindle guide section 3 is curved may be employed. The spindle guide section 3 may be of either a shape, in which the entirety thereof is curved at the same curvature, or a shape in which the curvature changes partially. Also, only a portion thereof may be of a curved shape. In such case, the remote controlled actuator 80 in its entirety may be replaced, but only the spindle guide section 3 and up there may be replaced. In the case of this embodiment, since the spindle guide section 3 is detachable relative to the drive unit housing 4a, replacement of the spindle guide 3 and up there is easy.

Even the remote controlled actuator 80 having the curved spindle guide section 3 is of a structure basically similar to that shown in and described with reference to FIGS. 3A to 4B in connection with the previously described first embodiment of the present invention in which the spindle guide section 3 has been shown and described as straight in shape, except for the difference in shape of the spindle guide section 3. It is, however, to be noted that where the spindle guide section 3 is of a curved shape, the outer shell pipe 25, the guide pipe 30 and the reinforcement shafts 34 have to be also curved. Also, the rotary shaft 22 is preferably made of a material easy to deform and, for example, a shape memory alloy is a suitable material for the rotary shaft 22.

FIG. 7 illustrates a third preferred embodiment of the present invention, in which the support device 81 is of a structure different from that has been described above. The support device 81 for the remote controlled work robot according to the third preferred embodiment of the present invention is made up of a fixture 95, secured to a ceiling 94 defines a base, and a translator unit 96 positioned below the fixture 95 for movement up and down relative to the fixture 95, and the remote controlled actuator 80 is mounted on the translatory unit 96 through the mounting stand 90. In other words, the support device 81 has one-degree-of-freedom system having only one degree of freedom in an up and down direction. A drive source 96a for driving the translatory unit 96, which forms a movable unit, is controlled by a support device controller 97 for the one-degree-of-freedom system. It is, however, to be noted that the fixture 95 of the support device 81 may not be necessary secured directly to the ceiling 94, but may instead be secured to the ceiling 94 through a mounting member (not shown). In such case, the mounting member will define the base.

Figure 8:
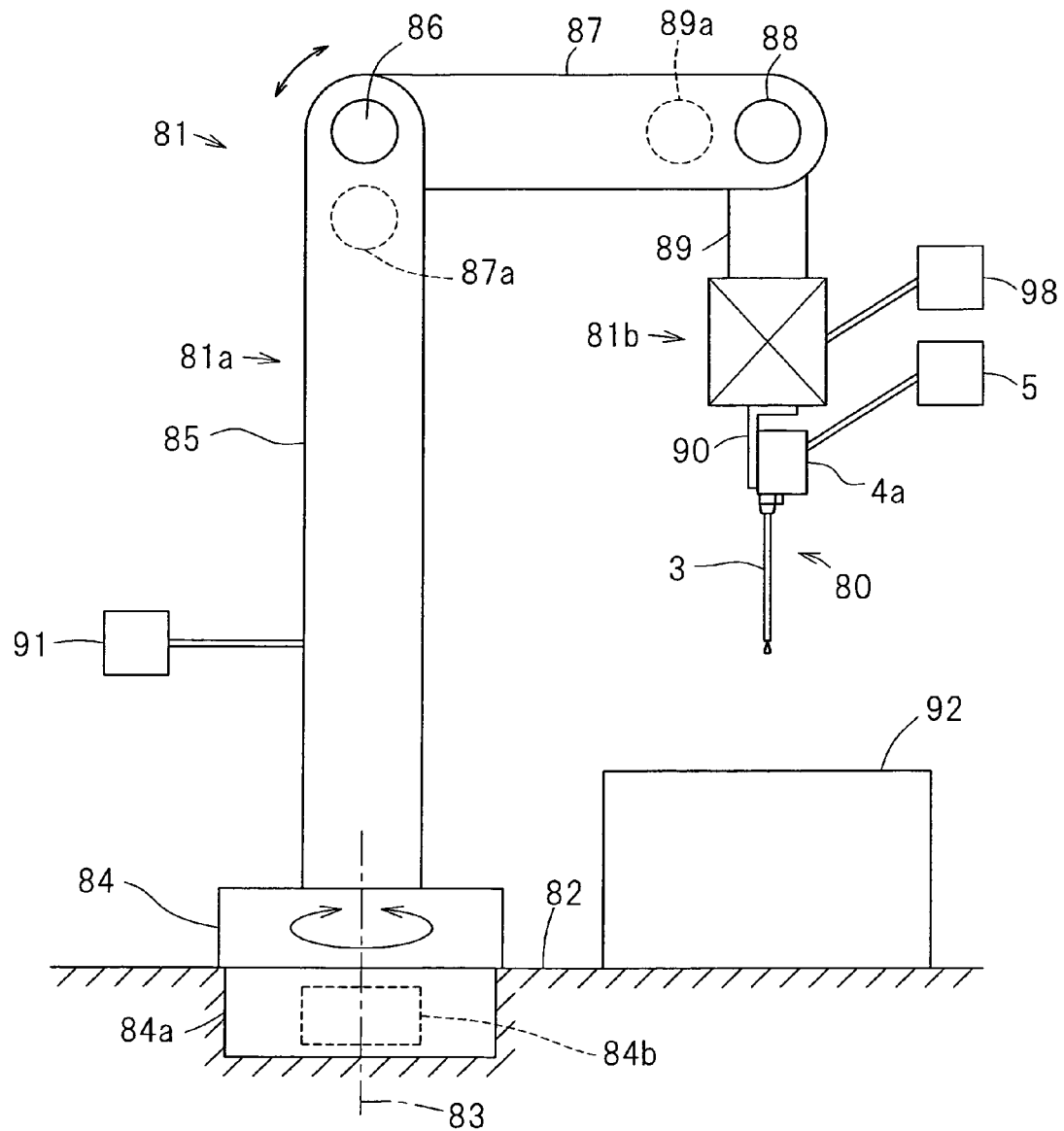
FIG. 8 is a diagram showing a schematic structure of the remote controlled work robot according to a fourth preferred embodiment of the present invention.

A fourth preferred embodiment of the present invention, in which the support device 81 of a further different structure is employed, is shown in FIG. 8, reference to which will now be made. The support device 81 for the remote controlled work robot according to the fourth embodiment of the present invention is made up of a three-degrees-of-freedom system 81a of a structure similar to the support device 81, shown in and described with reference to FIGS. 1 and 5, and a small sized multi-degrees-of-freedom system 81b provided in the pivot arm 89 of the three-degrees-of-freedom system 81a, and the remote controlled actuator 80 is mounted supported by the small sized multi-degrees-of-freedom system 81b through the mounting stand 90. The small sized multi-degrees-of-freedom system 81b may be any type provided that it has a plurality of degrees of freedom and is not therefore specifically limited to that shown and described. However, for the small sized multi-degrees-of-freedom system 81b, a mechanism of a high degree of mechanism or a mechanism having a wide working range or a mechanism such as, for example, a parallel link mechanism (not shown) comprised of, for example, a plurality of link mechanisms, or a link actuating device 100 (FIG. 11 to 13) or 200 (FIGS. 15 to 21) as will be described in detail later can be suitably employed. The small sized multi-degrees-of-freedom system 81b is controlled by a support device controller 98 for the small sized degree-of-freedom system, which is separate from the support device controller 91 for the previously described three-degrees-of-freedom system.

If as described above the support device 81 is constructed by combining the three-degrees-of-freedom system 81a and the small sized degree-of-freedom system 81b together, the unsubtle position and attitude of the remote controlled actuator 80 can be determined by the three-degrees-of-freedom system 81a and, on the other hand, the meticulous position and attitude of the remote controlled actuator 80 can be determined by the small sized degree-of-freedom system 81b. Accordingly, a subtle and delicate operation such as taking place when the skilled surgeon manually operates the remote controlled actuator 80 can be performed, thus enabling the meticulous processing to be accomplished.

Figure 9:
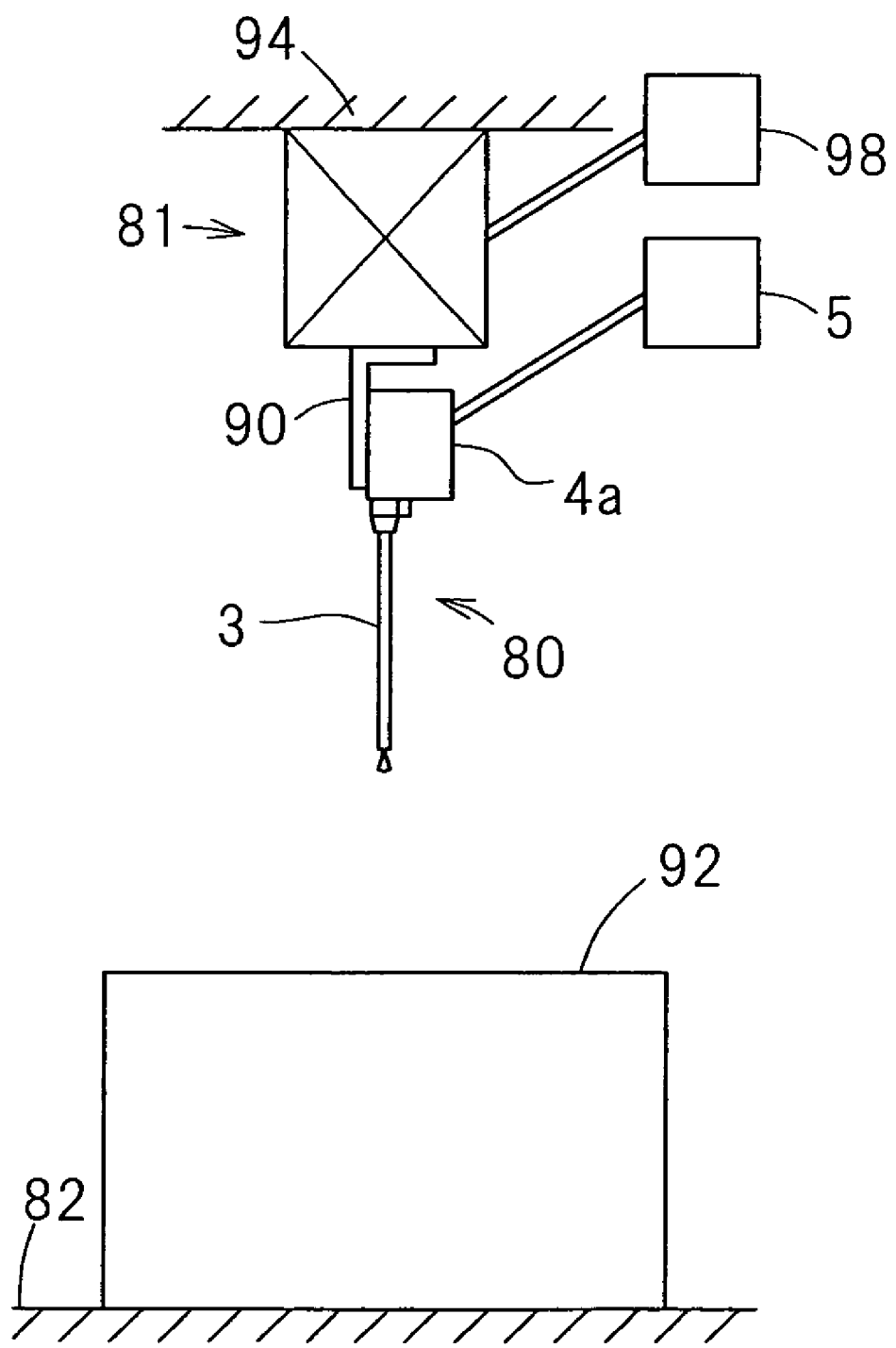
FIG. 9 is a diagram showing a schematic structure of the remote controlled work robot according to a fifth preferred embodiment of the present invention.

FIG. 9 illustrates a fifth preferred embodiment of the present invention utilizing the support device 81 of a yet different structure. The support device 81 used in the remote controlled work robot according to the fifth embodiment is itself of the small size multi-degrees-of-freedom system of the structure similar to the small size multi-degrees-of-freedom structure shown in and described with particular reference to FIG. 8 and, hence, the support device 81 secured to the ceiling 94, defining the base, and the remote controlled actuator 80 is supported by this support device 81 through the mounting stand 90. The support device 81, which is the small sized multi-degrees-of-freedom system, is controlled by the support device controller 98 for the small sized multi-degrees-of-freedom system. It is, however, to be noted that the support device 81 may be secured to the ceiling 94 through a suitable mounting member (not shown) instead of being secured directly to the ceiling 94. In such case, the mounting member defines the base.

Figure 10:
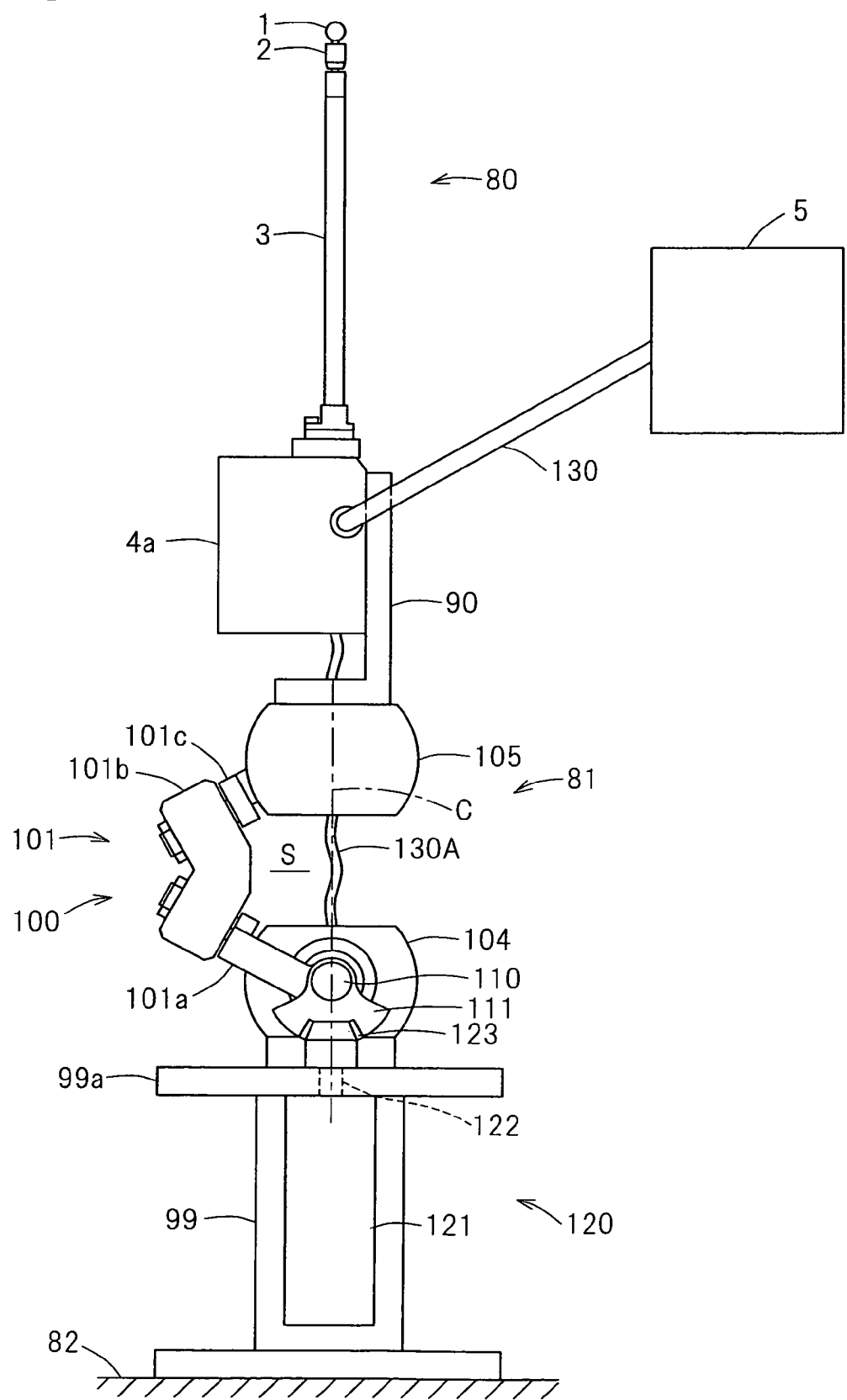
FIG. 10 is a diagram showing a schematic structure of the remote controlled work robot according to a sixth preferred embodiment of the present invention, which robot is provided with a support device comprised of, for example, a link actuating device.
Figure 11:
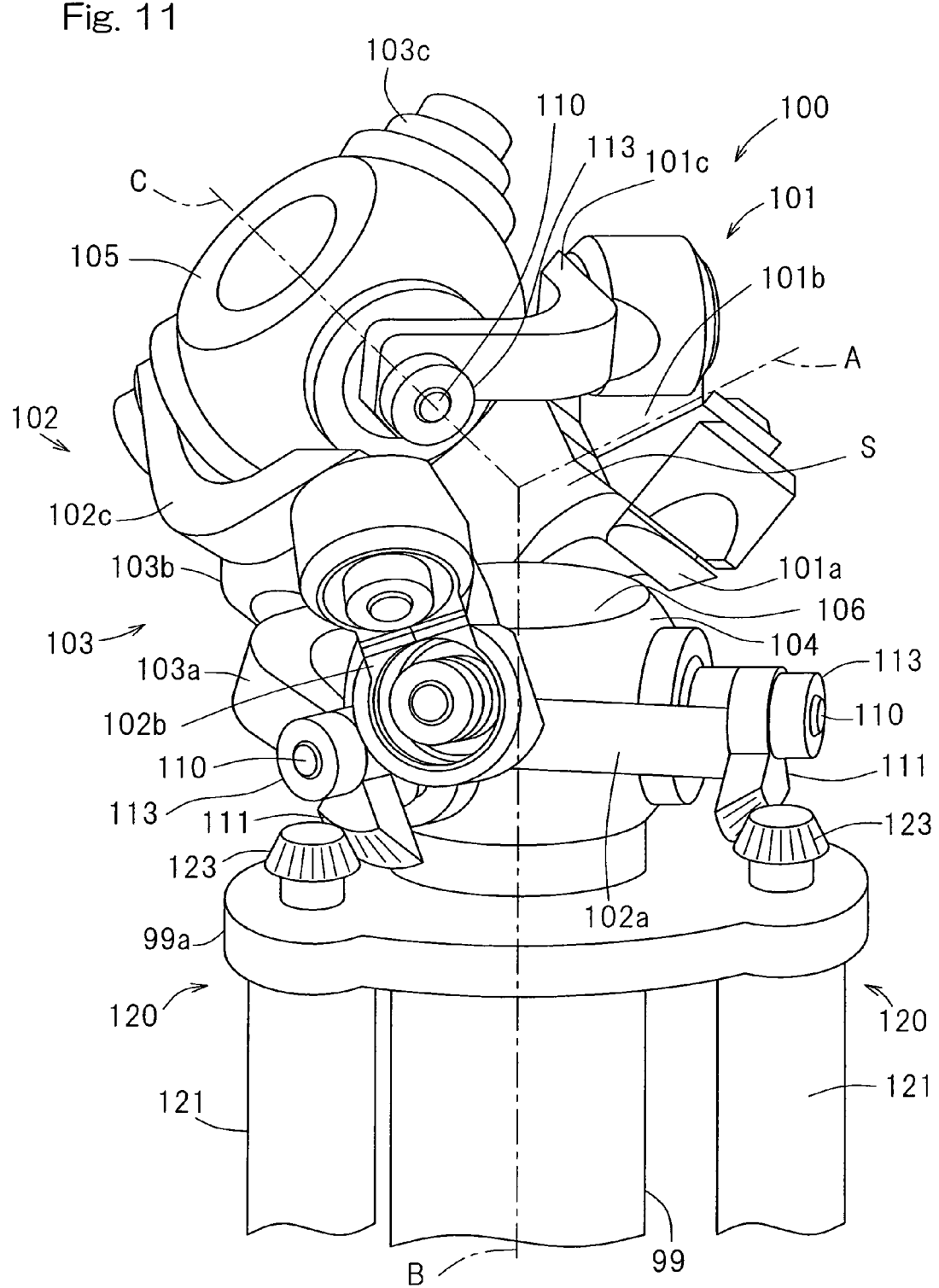
FIG. 11 is a perspective view showing the link actuating device.

The link actuating device used as the small sized multi-degrees-of-freedom system will now be described. FIG. 10 illustrates a schematic structural diagram of the remote controlled work robot according to a sixth preferred embodiment of the present invention, in which the multi-degrees-of-freedom system thereof is constituted by the link actuating device, and FIG. 11 illustrates a perspective view of such link actuating device 100. As best shown in FIG. 10, the support device 81 is made up of a pedestal 99 for the support thereon of the link actuating device 100. The pedestal 99 is installed on a floor surface 82 which defines the base.

As best shown in FIG. 11, the link actuating device 100 includes three sets of link mechanisms 101, 102 and 103 (hereinafter, designated by "101 to 103"). FIG. 10 illustrates only one of the sets the link mechanisms, for example, the link mechanism 101. Those three sets of the link devices 101 to 103 are of a geometrically identical shape. An input side of those link mechanisms 101 to 103 is mounted on the pedestal 99 whereas an output side thereof is secured to the drive unit housing 4a for the remote controlled actuator 80 through the mounting stand 90. In the instance as shown, the remote controlled actuator 80 is so supported that the rotary shaft 22, best shown in FIGS. 3A to 3C, of the remote controlled actuator 80 may be aligned with the center axis C of the link actuating device 100. The center axis C of the link actuating device 100 itself is the center axis C of an output member 105 as will be described later.

Each of the link mechanisms 101, 102 and 103 is comprised of an end link member 101a, 102a or 103a (hereinafter, designated by "101a to 103a") on the input side, an intermediate link member 101b, 102b or 103b (hereinafter, designated by "101b to 103b") and an end link member 101c, 102c or 103c (hereinafter, designated by "101c to 103c") on the output side and forms a three joint chained link mechanism having four turning pairs. The end link members 101a to 103a and 101c to 103c are of a spherical link structure and respective spherical surface link centers of the three sets of the link mechanisms 101 to 103 are aligned with each other and, also, the respective distances from their centers are equal to each other. Axes of the turning pair, which defines a connection between the end link members 101a to 103a and 101c to 103c and the intermediate link members 101b to 103b may have a certain crossed axes angle or parallel to each other. It is, however, to be noted that the respective shapes of the intermediate link members 101b to 103b in the three set of the link mechanisms 101 to 103 are geometrically identical with each other.

One set of the link mechanisms 101 to 103 includes an input member 104 mounted on the pedestal 99, an output member 105 mounted on the mounting stand 90, two end link members 101a to 103a and 101c to 103c for rotatably connecting the input member 104 and the output member 105 together, and an intermediate link member 101b to 103b rotatably connected with the opposite end link members 101a to 103a and 101c to 103c for connecting the opposite end link members 101a to 103a and 101c to 103c together.

The link mechanism 101 to 103 employed in the practice of this embodiment of the present invention is of a rotation symmetrical type, and respective relations in position between the input member 104 and the end link member 101a to 103a and between the output member 105 and the end link member 101c to 103c are so chosen as to be rotation symmetrical with each other about the center axis A of the intermediate link member 101b to 103b. In the instance as shown in FIG. 11, the center axis C of the output member 105 relative to the center axis B of the input member 104 is shown to be in a condition assuming a predetermined working angle.

Figure 12:
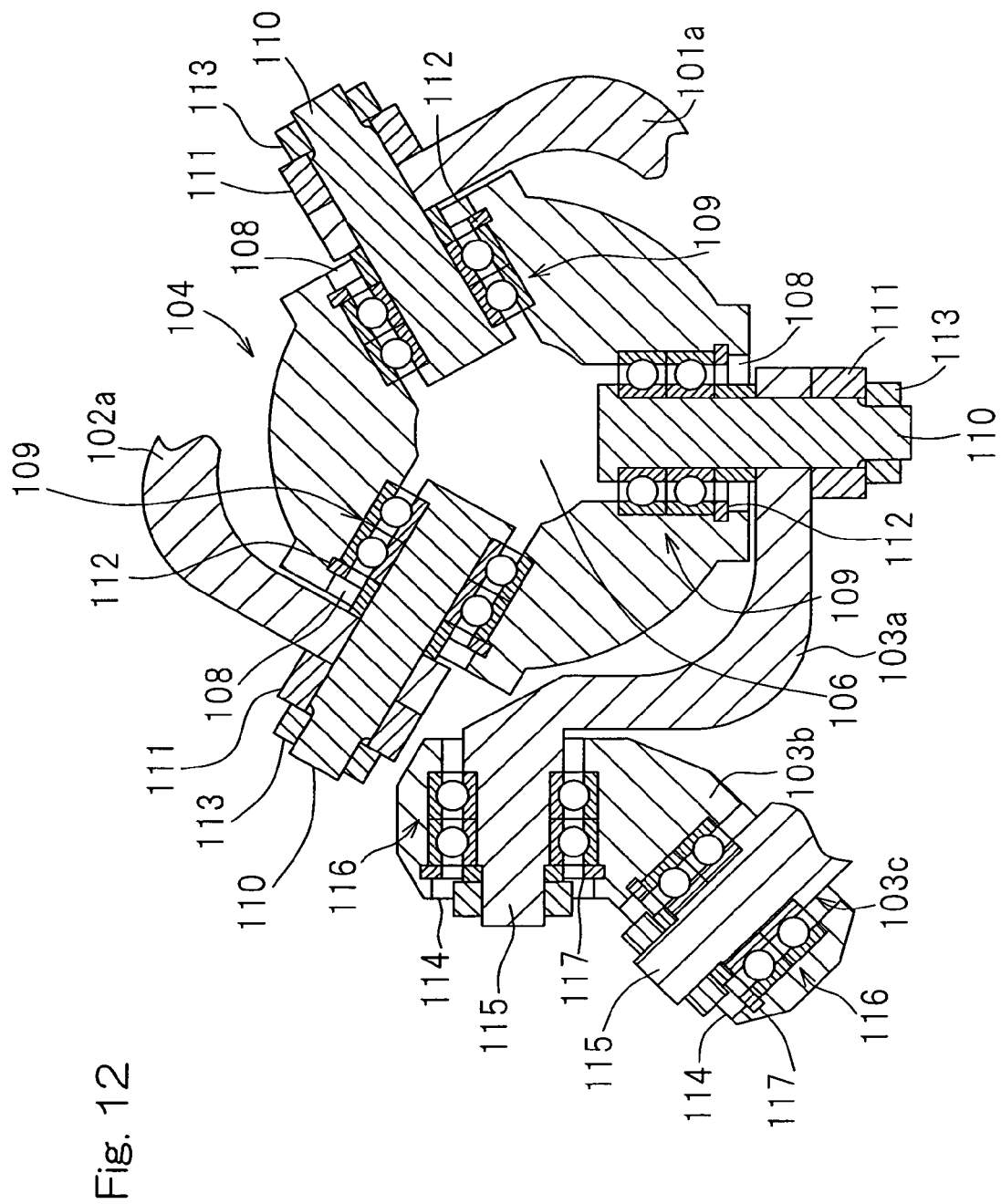
FIG. 12 is a sectional view showing an input member, an end link member on an input side and an intermediate link member all employed in the link actuating device.

As shown in FIG. 12, the input member 104 is of a structure having a center hole 106 defined therein as a passage for a wiring in an axial direction thereof, representing an annular shape with its outer shape being a spherical shape so that a large angle can be assumed, having a throughhole 108 defined therein in a radial direction having been spaced an equal distance from each other in a circumferential direction thereof, and having a spindle member 110 inserted into the throughhole 108 through bearings 109.

The bearing 109 is made up of a bearing outer ring accommodated within the throughhole 108 of the input member 104, a bearing inner ring mounted on the spindle member 110, and a plurality of rolling elements such as, for examples, balls that are rotatably interposed between the bearing outer ring and the bearing inner ring. The spindle member 110 has an outer end protruding outwardly from the input member 104, and the end link members 101a, 102a and 103a and a gear member 111 are mounted on a projected end portion of the spindle member 110 for rotation together therewith and are fixed in position by means of fastening of a nut 113 with a predetermined preload applied to the bearing 109. The gear member 111 forms a part of an angle control mechanism 120, as will be described later, for the link mechanism 101 to 103. A bearing 109 for rotatably supporting the spindle member 110 relative to the input member 104 is retained in position by a detent ring 112 so that it will not detach from the input member 104.

It is to be noted that the spindle member 110 and the end link members 101a to 103a and the gear member 111 are connected by means of a crimping technique. They may, however, be connected by means of keys or serrations. In such case, loosening of the connecting structure can be prevented and the transmission torque can be increased.

In view of the fact that the gear member 111 is provided on an outer end portion of the spindle member 110, a large inner space S such as shown in FIG. 10 is formed inside the link mechanism 101 to 103 and the center hole 106 of the input member 104. This inner space S is effectively utilized as a means for securing a space for installation of a passage for the flow of a control medium between input and output. More specifically, a wiring 130 connecting between the remote controlled actuator 80 and the actuator controller 5 is provided through this inner space S. In FIG. 10, for the purpose of convenience, the wiring 130 is shown as provided outside the inner space S, but in practice it is arranged at a position indicated by reference numeral 130A.

For the bearing 109, other than that two ball bearings are arranged as shown in FIG. 12, an angular ball bearing, a roller bearing or a slide bearing can be employed. It is to be noted that the output member 105 best shown in FIG. 10 is of a structure identical with the input member 104 except that the gear member 111 is provided on the outer end portion of the spindle member 110. Although the circumferential positions of the spindle members 110 may not be equidistantly spaced, it is necessary that input member 104 and the output member 105 must have a positional relation in the same circumferential direction. The input member 104 and the output member 105 are commonly shared by the three sets of the link mechanisms 101 to 103 with the end link members 101a to 103a and 101c to 103c coupled with the respective spindle members 110.

As shown in FIG. 11, each of the end link members 101a to 103a and 101c to 103c is of an L-shaped configuration having one side connected with the spindle member 110 and the other side connected with the intermediate link member 101b to 103b. The end link member 101a to 103a and 101c to 103c is of such a shape that in order to secure a large angle a bent base end inner side of a spindle portion 115, which is positioned on a link center side, is cut considerably.

The intermediate link member 101b to 103b is of a substantially L-shaped configuration having its opposite sided formed with respective throughholes 114. This intermediate link member 101b to 103b is of such a shape that in order to secure a large angle a peripheral side face thereof is cut. The spindle portion 115 formed integrally therewith so as to bend from the other side of the end link members 101a to 103a and 101c to 103c is inserted into the throughhole 114 on the opposite sides of the intermediate link member 101b to 103b through bearings 116.

Each of the bearings 116 is made up of a bearing outer ring engaged within the throughhole 114 in the intermediate link member 101b to 103b, a bearing inner sing externally mounted on the spindle portion 115 of the end link members 101a to 103a and 101c to 103c, and rolling elements such as, for example, balls interposed rollingly between the bearing outer ring and the bearing inner ring. The bearings 116 supporting the intermediate member 101b to 103b rotatably relative to the end link members 101a to 103a and 101c to 103c are retained by detent rings 117 so that they will not fall out of the corresponding throughholes 114.

In each of the link mechanisms 101 to 103 described hereinabove, the angle and the length of the spindle member 110 in each of the input and output members 104 and 105 and the geometric shape of the end link members 101a to 103a and 101c to 103c are equal on the input side and the output side, and the respective shapes of the intermediate link member 101b to 103b on the input side and that on the output side are similar to each other. Under these geometric conditions, if the angular positional relation between the intermediate link member 101b to 103b and the end link members 101a to 103a and 101c to 103c, which is connected with the input and output members 104 and 105, relative to a plane of symmetry of the intermediate link member 101b to 103b remain the same on the input side and the output side, the input member 104 and the end link member 101a to 103a and the output member 105 and the end link member 101c to 103c move in the same way in view of the geometric symmetry and the input side and the output side revolve at equal speed through the same angle of revolution. The plane of symmetry of the intermediate link member 101b to 103b, when revolving at the equal speed, is referred to as an isokinetic isosceles plane.

For this reason, when a plurality of the link mechanisms 101 to 103 of the same geometrical shape commonly sharing the input and output members 104 and 105 are arranged on the circumference, as the position at which the plural link mechanisms 101 to 103 can move with no contradiction the intermediate link member 101b to 103b is limited to the movement on the isokinetic isosceles plane, wherefore the isokinetic revolution can be obtained even if the input side and the output side take an arbitrarily chosen operating angle.

Respective points of rotation of the four turning pairs in each of the link mechanisms 101 to 103, that is, two points of connection between the end link members 101a to 103a and 101c to 103c and the input and output members 104 and 105, and two points of connection between the end link member 101a to 103a and 101c to 103c and the intermediate link member 101b to 103b are so designed and so configured as to represent a bearing structure. Accordingly, it is possible to reduce the rotational resistance while suppressing the frictional resistance at those points of rotation and not only can a smooth power transmission be secured, but also the durability can be increased.

In this bearing structure, when a preload is applied, a radial gap and a thrust gap can be eliminated to thereby suppress an undesirable rattling motion at the connection and not only can a rotational phase difference between input and the output be eliminated to maintain the isokinetic property, but an undesirable generation of vibrations and noises can also be suppressed. In particular, in the bearing structure referred to above, rendering the bearing gap to be a negative gap is effective to minimize a backlash occurring between the input and the output.

The link actuating device 100 referred to above is so designed and so configured as to control the attitude of two degrees of freedom of the input member 105 by controlling the angle of the end link member 101a to 103a on the input side relative to the input member 104 with respect to the two or more link mechanisms of the link mechanisms 101 to 103. In the instance as shown in and described with reference to FIGS. 10 to 12, the angle of the end link member 101a to 103a of all of the link mechanisms 101 to 103 is controlled. The angle control mechanism 120 for the end link member 101a to 103a is of a structure in which as shown in FIG. 11, a link mechanism drive source 121 is provided in an upper flange 99a of the pedestal 99 so as to be oriented downwardly, a bevel gear 123 is mounted on an output shaft 122 of the link mechanism drive source 121, which protrudes upwardly from the upper flange 99a, and a threaded portion of the gear member 111 fitted to the spindle member 110 of the input member 104 is engaged with the bevel gear 123. The link mechanism drive source 121 is employed in the form of, for example, an electrically operated motor. When the link mechanism drive source 121 is driven, the rotation thereof is transmitted to the spindle member 110 through the bevel gear 123 then meshed with the gear member 111 and, accordingly the end link member 101a to 103a changes its angle relative to the input member 104.

According to the link actuating device 100 of the structure described above, the operating range of the output member 105 relative to the input member 104 can be made large. For example, it is possible to make the maximum bending angle between the center axis B of the input member 104 and the center axis C of the output member 105 to be about ±90°. Also, the angle of swivel of the output member 105 relative to the input member 104 can be set to a value within the range of 0 to 360°. In view of the fact that the link mechanism drive source 121 for controlling the attitude of the output member 105 arbitrarily is provided in the turning pair of each of the link mechanisms 101 to 103 coupled with the input member 104, the output member 105 can be easily set to an arbitrary attitude. Since the force is transmitted at a constant speed from the input member 104 to the output member 105, the operation of the output member 105 takes place smoothly. Although in the illustrated embodiment now under discussion, the turning pair of the input member 104 and each set of the link mechanisms 101 to 103 is provided with the link mechanism drive source 121, the use of two or more sets of the link mechanism drive sources 121 will make it possible to determine the attitude of the output member 105 relative to the input member 104.

Also, since the link mechanism 101 to 103 and the link mechanism drive source 121 are provided separately, a portion of the weight of the link mechanism 101 to 103 can be reduced. Since the link mechanism drive source 121 is separated a distance from the remote controlled actuator 80 with the link mechanisms 101 to 103 intervening therebetween, the link mechanism drive source 121 can be installed spaced a substantial distance from the patient particularly where the remote controlled work robot of the present invention is used in the medical field. For this reason, if the link mechanism drive source 121 is enclosed with a covering or the like, there is no need to sterilize the link mechanism drive source 121. In other words, the link mechanism drive source 121 may not be provided with a complicated sealing structure and the structure can therefore be simplified.

Also, since the link actuating device 100 of the structure described above is such that the bearing outer ring is included in the input and output members 104 and 105 and the bearing inner ring is coupled with the end link members 101a to 103a and 101c to 103c with the bearing structure embedded in the input and output members 104 and 105, respective contours of the input and output members 104 and 105 can be expanded without the contour of the apparatus in its entirety being increased. Accordingly, a space for installation on the input side and the output side relative to the pedestal 99 and the mounting stand 90 can be secured easily. In addition, when the wiring 130 connecting between the remote controlled actuator 80 and the actuator controller 5 is passed through and provided in the inner spaces S of the link mechanisms 101 to 103, the wiring 130 can be easily laid and will not constitute any obstruction.

Figure 13:
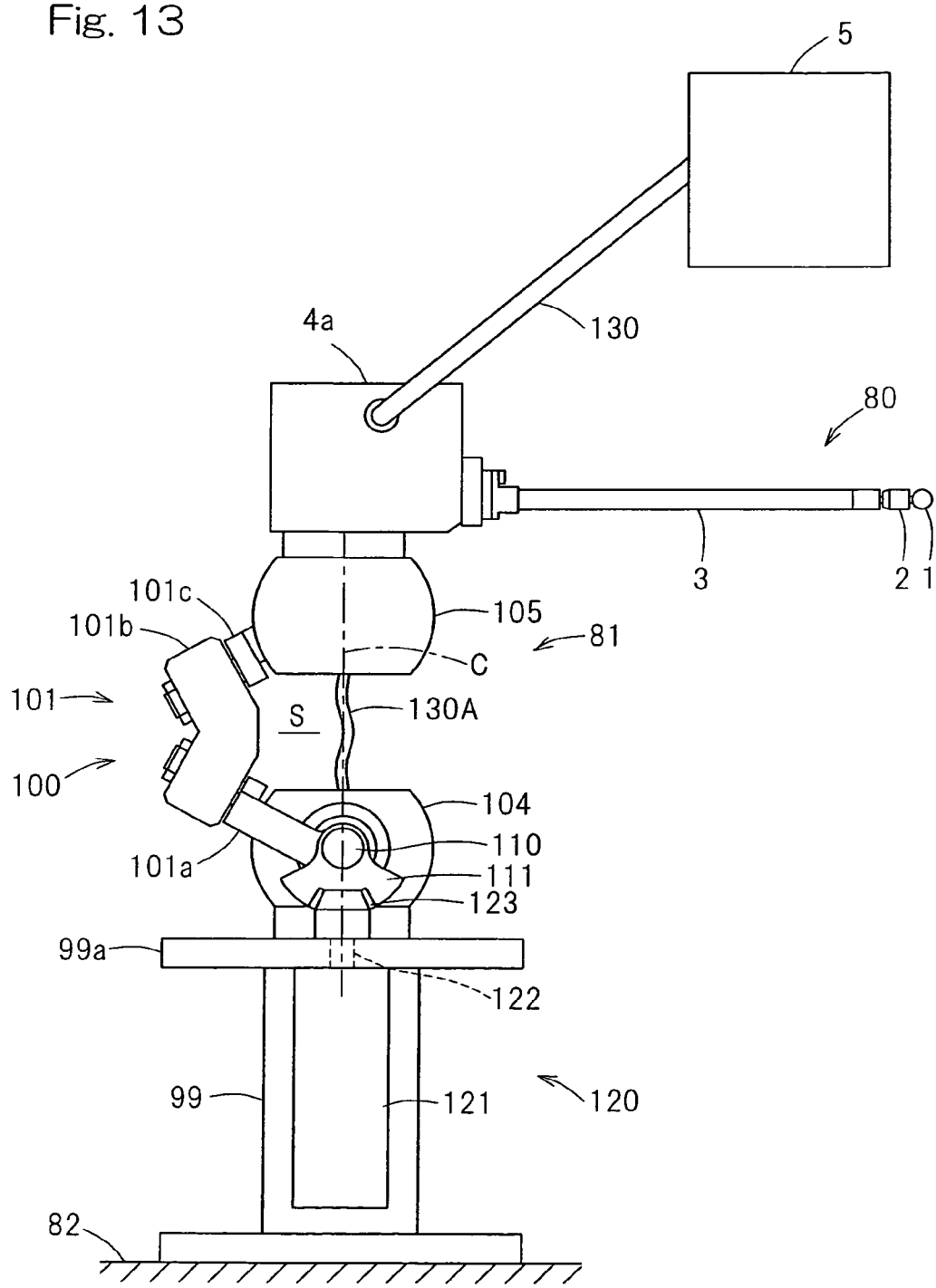
FIG. 13 is a diagram showing a schematic structure of the remote controlled work robot according to a seventh preferred embodiment of the present invention, in which the remote controlled actuator is mounted in an orientation different from that of the remote controlled actuator employed in the work robot according to the sixth embodiment of the present invention shown in FIG. 10.

Although in FIG. 10, the direction of the rotary shaft 22 (best shown in FIG. 3A) of the remote controlled actuator 80 has been shown and described as aligned with the center axis C (the center axis of the output member 105) of the link actuating device 100, the remote controlled actuator 80 may be so supported that the rotary shaft 22 may extend in a direction perpendicular to the center axis C of the link actuating device 100 as shown in FIG. 13 in connection with a seventh preferred embodiment of the present invention. Also, the drive unit housing 4a of the remote controlled actuator 80 may be directly fitted to the output member 105 with no mounting stand 90 intervened therebetween.

Figure 14:
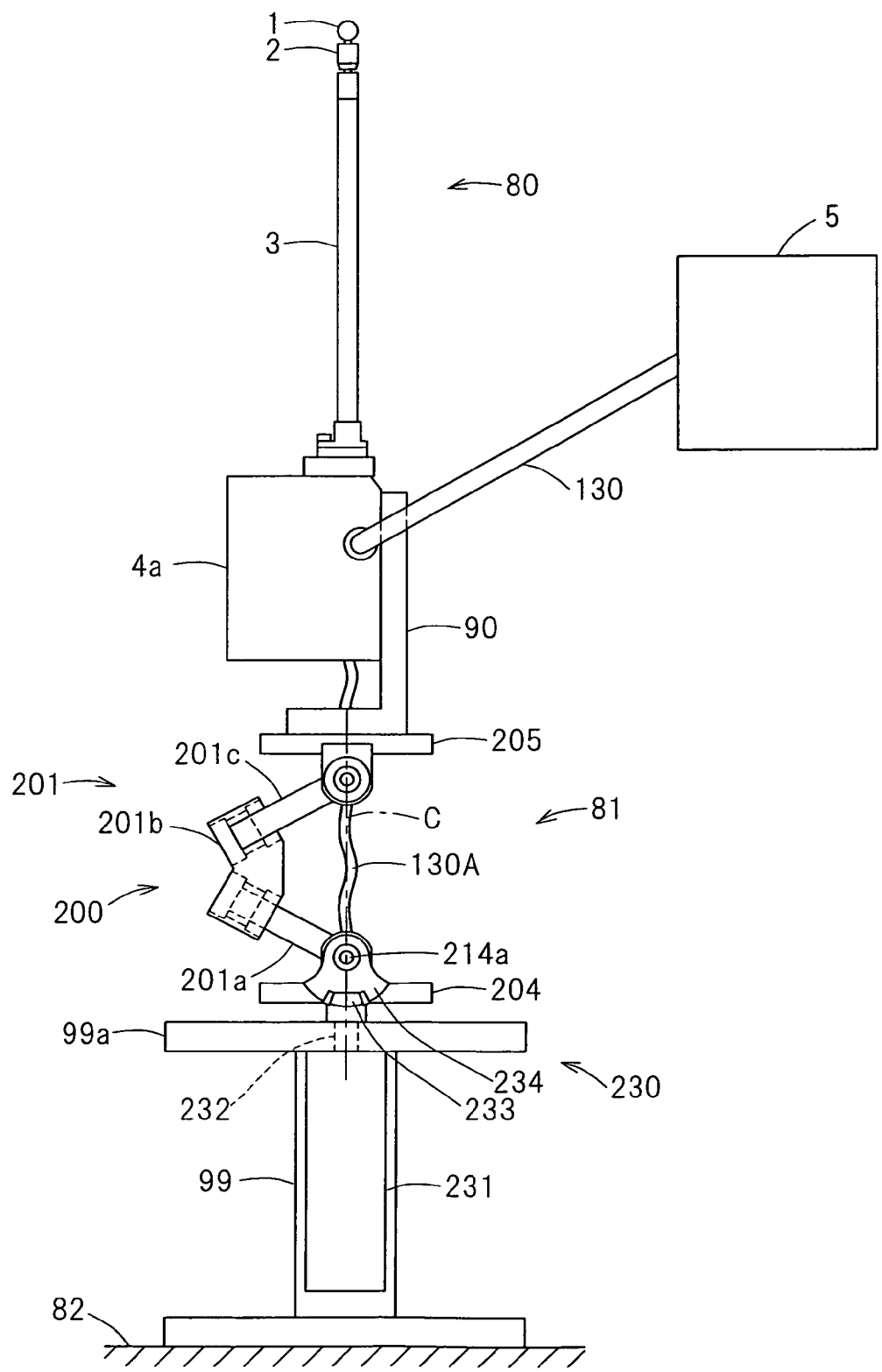
FIG. 14 is a diagram showing a schematic structure of the remote controlled work robot according to an eighth preferred embodiment of the present invention, which robot is provided with the support device comprised of a different link actuating device.
Figure 15:
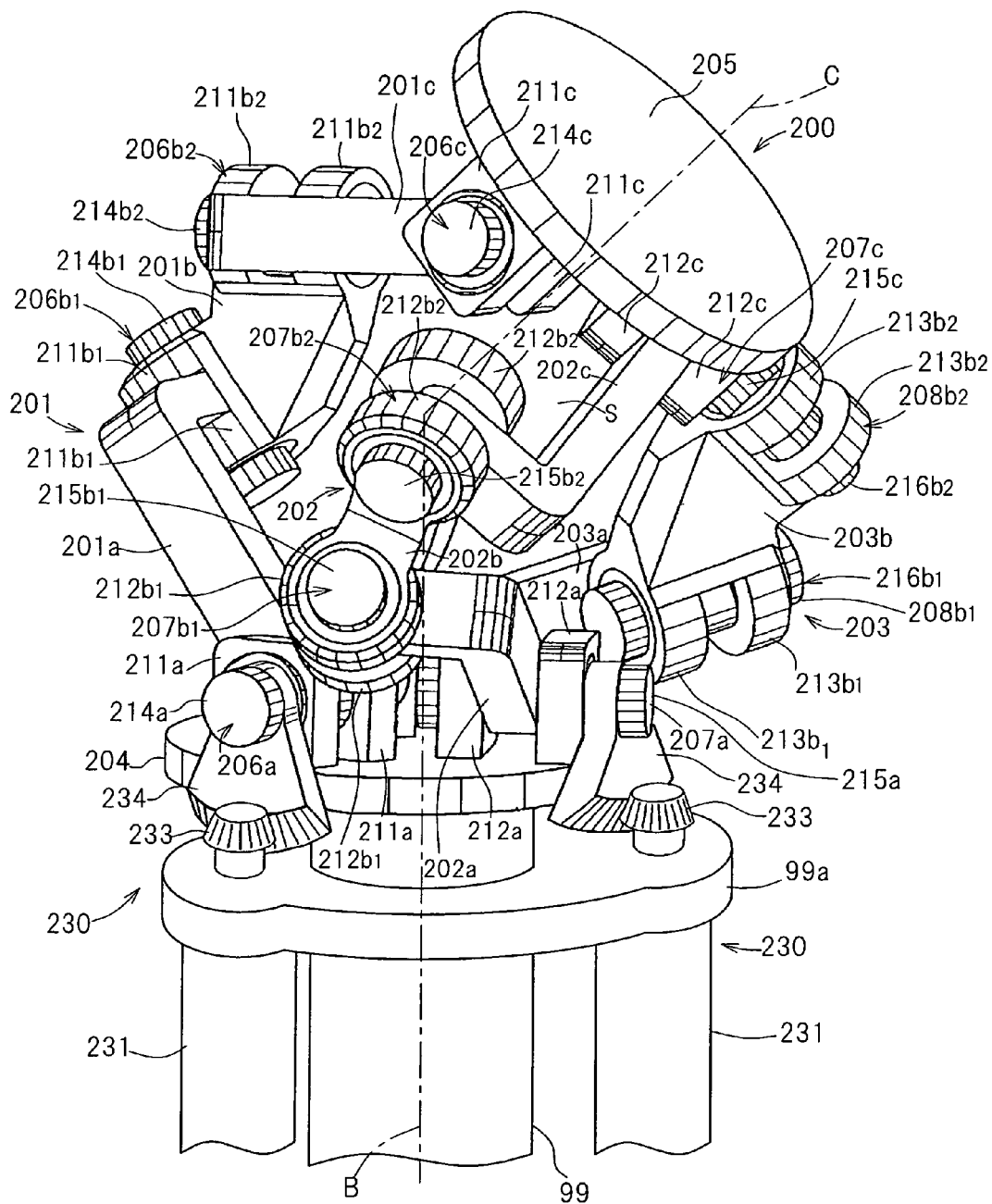
FIG. 15 is a perspective view of the different link actuating device.

FIG. 14 illustrates a schematic structural diagram of the remote controlled work robot designed in accordance with an eighth preferred embodiment of the present invention, in which the support device has one multi-degree-of-freedom systems which is constituted with the link actuating device or the like of a different structure, and FIG. 15 is a perspective view of the link actuating device therefor. The support device 81 is made up of a link actuating device, now identified by 200, and a pedestal 99 on which the link actuating device 200 is mounted. The pedestal 99 is installed on the floor surface 82 which defines the base.

The link actuating device 200 is provided with three sets of link mechanisms 201, 202 and 203 (hereinafter, designated by "201 to 203"). It is, however, to be noted that only one set of the link mechanism 201 is shown in FIG. 14. Those three sets of the link devices 201 to 203 are geometrically identical in shape with each other. The link mechanism 201 to 203 has an input side mounted on the pedestal 99 and also has an output side fitted to the drive unit housing 4a for the remote controlled actuator 80 through the mounting stand 90. In the instance as shown, the remote controlled actuator 80 has its rotary shaft 22 (best shown in FIG. 3A) supported so as to align with the center axis C (the center axis of the output member 205) of the link actuating device 200.

Figure 16:
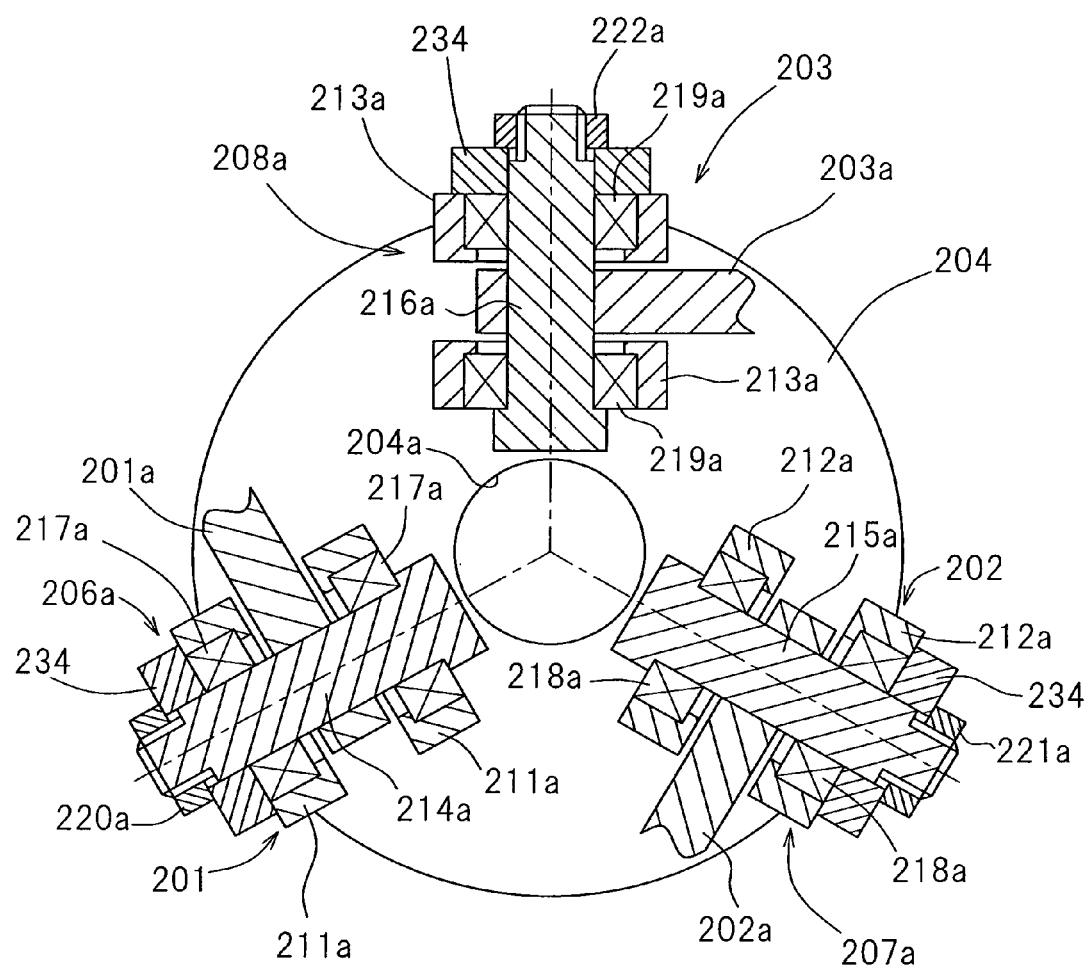
FIG. 16 is a sectional view showing a turning pair mechanism between the input member and an end link member on the input side, both employed in the different link actuating device.

Each of the link mechanisms 201, 202 and 203 is made up of an input side end link member 201a, 202a or 203a (hereinafter, designated by "201a to 203a") connected rotatably with the input member 204 of a disc-like shape, an output side end link member 201c, 202c or 203c (hereinafter, designated by "201c to 203c") connected rotatably with the output member 205 of a disc-like shape, and an intermediate link member 201b, 202b or 203c connected rotatably with the opposite end link members 201a to 203a and 201c to 203c and connecting the opposite end link members 201a to 203c and 201c to 203c together, and forms a three joint chained link mechanism comprised of four turning pairs 206a, 207a and 208a (hereinafter, designated by "206a to 208a"), $206b_1$, $207b_1$ and $208_1$ (hereinafter, designated by "$206b_1$ to $208b_1$") $206b_2$, $207b_2$ and $208b_2$ (hereinafter, designated by "$206b_2$ to $208b_2$") or 206c, 207c and 208c (hereinafter, designated by "206c to 208c"). It is to be noted that the turning pairs 208a and 208c are hidden and are not therefore visible in FIG. 15, but the turning pair 208a is shown in FIG. 16. The turning pair 208c is shown nowhere, but for the purpose of description, the reference numeral is employed in this specification.

The end link members 201a to 203a and 201c to 203c are of a spherical link structure and respective spherical surface link centers of the three sets of the link mechanisms 201 to 203 are aligned with each other and, also, the respective distances from their centers are equal to each other. Axes of connection of the turning pairs $206b_1$ to $208b_1$ and $206b_2$ to $208b_2$ with the end link members 201a to 203a and 201c to 203c and the intermediate link members 201b to 203b may have a certain crossed axes angle or parallel to each other. It is, however, to be noted that the respective shapes of the intermediate link members 201b to 203b in the three set of the link mechanisms 201 to 203 are geometrically identical with each other.

The link mechanism 201 to 203 employed in the practice of this embodiment of the present invention is of a mirror symmetry type and respective positional relations between both of the input member 204 and the input side end link member 201a to 203a and both of the output member 205 and the output side end link member 201c to 203c are such as to form the mirror symmetry type with respect to the center line of the intermediate link member 201b to 203b. In FIG. 15, however, the condition is shown in which the output member 205 assumes a predetermined operating angle relative to the input member 204.

FIG. 16 illustrates the turning pair 206a to 208a of the input member 204 and the input side end link member 201a to 203a. A pair of support members 211a, 212a and 213a (hereinafter, designated by "211a to 213a") for each link mechanism 201 to 203 are disposed on a top surface of the input member 204 of the disc-like shape. The support members 211a to 213a represent a structure capable of being detachable relative to the input member 204 by means of, for example, screws or the like, but they may be formed integrally with the input member 204. One pair of the support members 211a to 213a have respective bearings 217a, 218a, 219a (hereinafter, designated by "217a to 219a") fitted thereto, and support rods 214a, 215a, 216a (hereinafter, designated by "214a to 216a") rotatably supported between the pair of the bearings 217a to 219a are connected with one arm end of the end link member 201a to 203a of an L-shaped configuration while interposed between the pair of the support members 211a to 213a. Also, a gear member 234 forming a part of an angle control mechanism 230 as will be described later is connected with respective outer sides of the pair of the support members 211a to 213a in the support rod 214a to 216a. The arm end of the end link member 201a to 203a and the gear member 234 are fixed to the respective support rod 214a to 216a by means of, for example, set screws.

Also, the support rod 214a to 216a has an outer end provided with a respective nut 220a, 221a, 222a (hereinafter, designated by "220a to 222a") theadingly mounted thereon and fastening of this nut 220a to 222a with the intervention of a spacer is effective to adjustably apply a predetermined amount of preload to the bearings 217a to 219a.

While the circumferential positions of the support members 211a to 213a may not be spaced an equal distance from each other, the input member 204 and the output member 205 must be held in the same circumferential positional relation to each other. The input member 204 and the output member 205 are commonly shared by the three sets of the link mechanisms 201 to 203 and the end link members 211a to 213a and 211c to 213c are connected with the support members 211a to 213a and 211c to 213c. Although the input member 204 and the output member 205 fitted to the support members 211a to 213a and 211c to 213c have been shown and described as having the disc-like configuration, they may be of any suitable shape provided that a sufficient mounting space for the support members 211a to 213a and 211c to 213c can be available. In the illustrated embodiment, however, both of the input and output members 204 and 205 are rendered to be of an perforated disc-like shape having a throughhole 204a (although a throughhole for the output member 205 is not shown) defined at the center thereof, and the wiring 130 (best shown in FIG. 14) for connecting the remote controlled actuator 80 and the actuator controller 5 together is provided through the throughholes 204a in the input and output members 204 and 205 and the inner space S of the link mechanism 201 to 203. In FIG. 14, for the purpose of convenience, the wiring 130 is shown as positioned outside the inner space S, but in practice it is positioned at a location indicated by a reference numeral 130A.

The turning pair 206c to 208c, which is a point of connection between the output member 205 and the output side end link member 201c to 203c, is of a structure identical with the turning pair 205a to 208a, which is a point of connection between the input member 204 and the input side end link member 201a to 203a and, therefore, the detail of the turning pair 206c to 208c are not reiterated for the sake of brevity.

In the turning pair $206b_1$ to $208b_1$ of the input side end link member 201a to 203a and one end of the intermediate link member 201b to 203b, the other end of the input side end link member 201a to 203a is connected with one end of the one end of the intermediate link member 201b to 203b of a substantially L-shaped configuration. The one end of the intermediate link member 201b to 203b is provided with a pair of support members $211b_1$ to $213b_1$. This pair of the support members $211b_1$ to $213b_1$ have respective bearings (not shown) fitted thereto and support rods $214b_1$, $215b_1$ and $216b_1$ (hereinafter, designated by "$214b_1$ to $216b_1$"), which are rotatably supported by the pair of the bearings, are connected with the other arm end of the L-shaped end link member 201a to 203a while having been inserted in between the pair of the support members $211b_1$ to $213b_1$. The support member $211b_1$ to $213b_1$ may be either a structure detachable relative to the intermediate link member 201b to 203b by means of, for example, a screw or of an integral structure.

It is to be noted that the arm end of the end link member 201a to 203a is fixed to the support rod $214b_1$ to $216b_1$ by means of a set screw. The fixing method thereof may be by means of keys or D-cut or the like other than the set screw. Also, end portions of the support rod $214b_1$ to $216b_1$ is rendered to be capable of adjusting a predetermined amount of preload by applying such preload to the bearing by intervening a spacer or the line with a nut having been fastened.

The turning pair $206b_2$ to $208b_2$, which is a point of connection between the other arm end of the output side end link member 201c to 203c and the other end of the intermediate link member 201b to 203b, is of the structure identical with the turning pair $206b_1$ to $208b_1$ between the other arm end of the previously described end link member 201a to 203a and the one end of the intermediate link member 201b to 203b and, therefore, the details thereof are not reiterated for the sake of brevity.

In the previously described link mechanism 201 to 203, the respective angles and lengths of the support rods 214a to 216a and 214c to 216c for the input and output members 204 and 205 and the geometrical shape of the end link member 201a to 203a are identical on the input side and on the output side and, also, the shape of the intermediate link member 201b to 203b are identical on the input side and on the output side, and if the angular positional relation between the intermediate link member 201b to 203b and the end link members 201a to 203a and 201c to 203c, which are connected with the input member 204 and the output member 205, relative to the plane of symmetry of the intermediate link member 201b to 203b is made identical on the input side and the output side. When this condition is established, the input member 204 and the input side end link member 201a to 203a and the output member 205 and the output side end link member 201c to 203c move in the same way in view of the geometric symmetry and the input side and the output side revolve at equal speed through the same angle of revolution. The plane of symmetry of the intermediate link member 201b to 203b, when revolving at the equal speed, is referred to as an isokinetic isosceles plane.

When a plurality of the link mechanisms 201 to 203 of the same geometrical shape which commonly share the input and output members 204 and 205 with each other are arranged on the circumference, as the position at which the plural link mechanisms 201 to 203 can move with no contradiction, the intermediate link member 201b to 203b can be limited to the movement on the isokinetic isosceles plane, wherefore the isokinetic revolution can be obtained even if the input side and the output side take an arbitrarily chosen operating angle.

The link actuating device 200 referred to above is so designed and so configured as to control the attitude of two degrees of freedom of the output member 205 by controlling the angle of the input side end link member 201a to 203a relative to the input member 204 with respect to the two or more link mechanisms of the link mechanisms 201 to 203. In the instance as shown in and described with reference to FIGS. 14 to 16, the angles of the end link members 201a to 203a of all of the link mechanisms 201 to 203 are controlled. The angle control mechanism 230 for the end link member 201a to 203c is of a structure in which as shown in FIG. 14, a link mechanism drive source 231 is provided in an upper flange 99a of the pedestal 99 so as to be oriented downwardly, a bevel gear 233 is mounted on an output shaft 232 of the link mechanism drive source 231, which protrudes upwardly from the upper flange 99a, and a threaded portion of the gear member 234 fitted to the spindle rod 214a to 216a of the input member 204 is engaged with the bevel gear 233. The link mechanism drive source 231 is employed in the form of, for example, an electrically operated motor. When the link mechanism drive source 231 is driven, the rotation thereof is transmitted to the support rod 214a to 216a through the bevel gear 233 then meshed with the gear member 234 and, accordingly the end link member 201a to 203a changes its angle relative to the input member 204.

According to the link actuating device 200 of the structure described above, the operating range of the output member 205 relative to the input member 204 can be made large. For example, it is possible to make the maximum bending angle between the center axis B of the input member 204 and the center axis C of the output member 205 to be about ±90°. Also, the angle of swivel of the output member 205 relative to the input member 204 can be set to a value within the range of 0 to 360°. In view of the fact that the turning pair 206a to 208a of the input member 204 and each of the link mechanisms 201 to 203 is provided with a link mechanism drive source 231 for controlling arbitrarily the output member 205, the output member 205 can be easily set to an arbitrary attitude. Since the force is transmitted at a constant speed from the input member 204 to the output member 205, the operation of the output member 205 takes place smoothly. Although in the illustrated embodiment now under discussion, the turning pair of the input member 204 and the link mechanism 201 to 203 is provided with the link mechanism drive source 231, the use of two or more sets of the link mechanism drive sources 231 will make it possible to determine the attitude of the output member 205 relative to the input member 204.

Also, since the link mechanism 201 to 203 and the link mechanism drive source 231 are provided separately, a portion of the weight of the link mechanism 201 to 203 can be reduced. Since the link mechanism drive source 231 is separated from the remote controlled actuator 80 a distance larger than the link mechanisms 201 to 203 intervening therebetween, the link mechanism drive source 231 can be installed spaced a substantial distance from the patient particularly where the remote controlled work robot of the present invention is used in the medical field. For this reason, if the link mechanism drive source 231 is enclosed with a covering or the like, there is no need to sterilize the link mechanism drive source 231. In other words, the link mechanism drive source 231 may not be provided with a complicated sealing structure and the structure can therefore be simplified.

In addition, when the wiring 130 connecting between the remote controlled actuator 80 and the actuator controller 5 is passed through and provided in the inner spaces S of the link mechanisms 101 to 103, the wiring 130 can be easily laid and will not constitute any obstruction.

When the four turning pairs 206a to 208a, $206b_1$ to $208b_1$, $206b_2$ to $208b_2$ and 206c to 208c in each of the link mechanisms 201 to 203, that is, a point of connection of the input member 204 with the input side end link member 201a to 203a, a point of connection of the input side end link member 210a to 203a with the intermediate link member 201b to 203b, a point of connection of the input side end link member 201a to 203a with the output side end link member 201c to 203c and a point of connection of the output side end link member 201c to 203c with the output member 205 are so designed and so configured to represent a bearing structure, the rotational reissuance can be reduced while the frictional resistance at each of those points of connection is suppressed, and, hence, not only can a smooth power transmission be secured, but the durability thereof can also be increased.

Also, in view of the fact that the bearings are arranged in the four rotational pairings 206a to 208a, $206b_1$ to $208b_1$, $206b_2$ to $208b_2$ and 206c to 208c of the link mechanism 201 to 203 so as to support the four rotational pairings 206a to 208a, $206b_1$ to $208b_1$, $206b_2$ to $208b_2$ and 206c to 208c at their opposite ends, the bearing rigidity can be increased. In addition, since component parts can become detachable relative to each other at any part other than the turning pairs, the assemblability can be increased. As a result of increase of the assemblability, downsizing of the link mechanism 201 to 203 can be easily realized.

Figure 17:
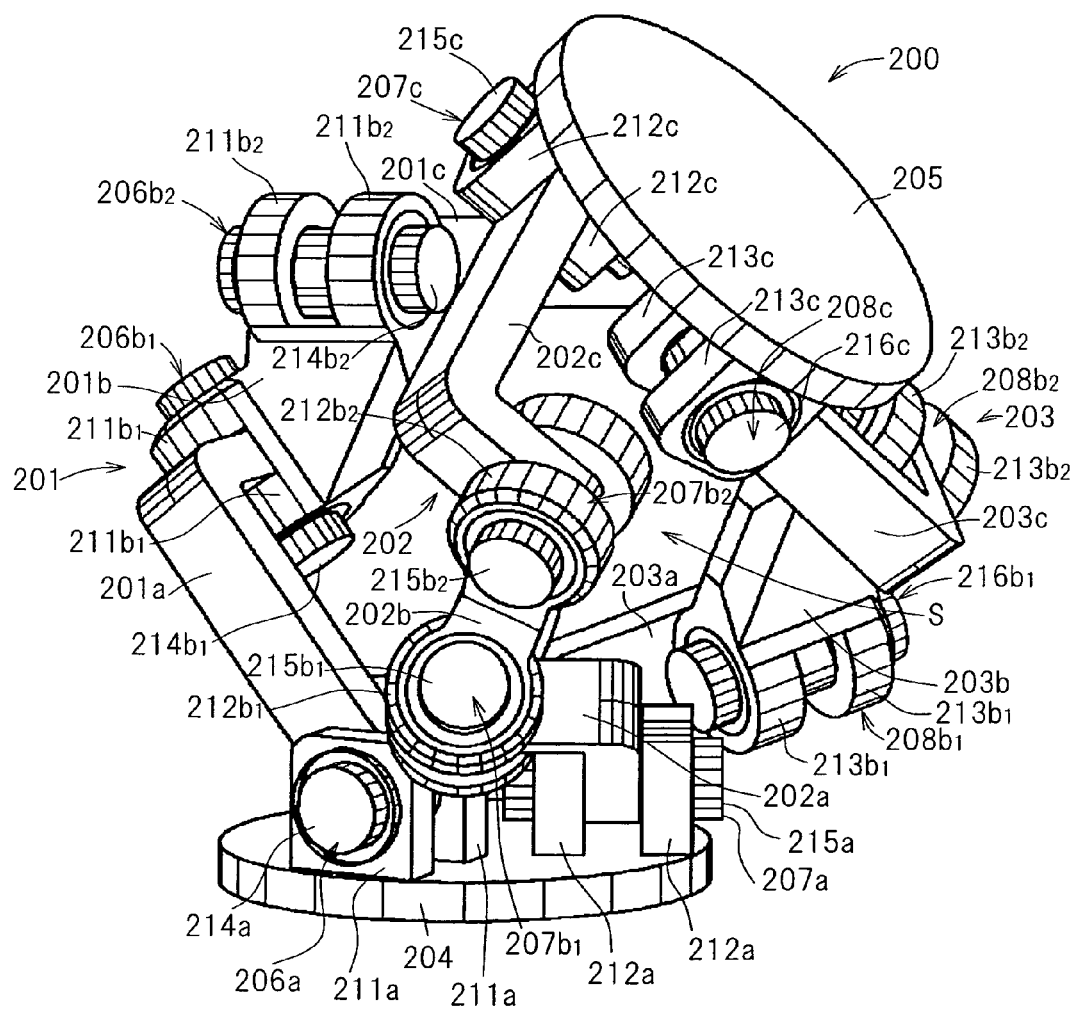
FIG. 17 is a perspective view showing the link actuating device according to a ninth preferred embodiment of the present invention.

The link mechanism 201 to 203 employed in the practice of the embodiment of the present invention shown in and described with reference to FIG. 15 is of a mirror symmetry type, but it may be of a rotation symmetry as is the case with a ninth preferred embodiment of the present invention shown in FIG. 17. The link mechanism 201 to 203 of the rotation symmetry type is such that the positional relation between both of the input member 204 and the end link member 201a to 203a and both of the output member 205 and the end link member 201 c to 203c is rotationally symmetrical with respect to the center line of the intermediate link member 201b to 203b. In the instance as shown in FIG. 17, the output member 205 is shown as assuming a predetermined operating angle relative to the input member 204. It is to be noted that FIG. 17 illustrates the link actuating device 200 in which no gear member 234 is provided in the support rod 214a to 216a that is supported by the input member 204.

Figure 18:
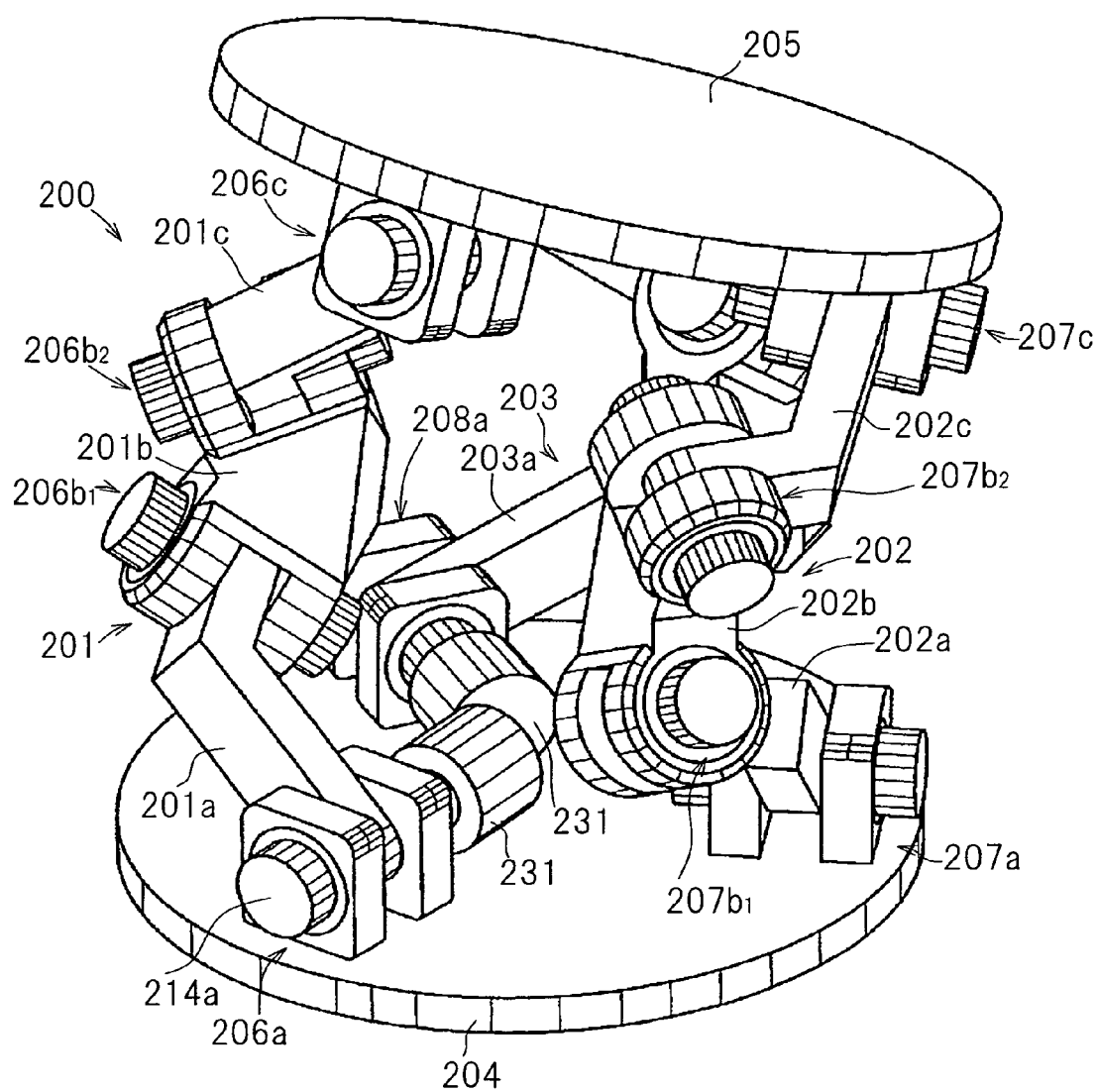
FIG. 18 is a perspective view showing an example of the link actuating device in the remote controlled work robot according to a tenth preferred embodiment of the present invention.
Figure 19:
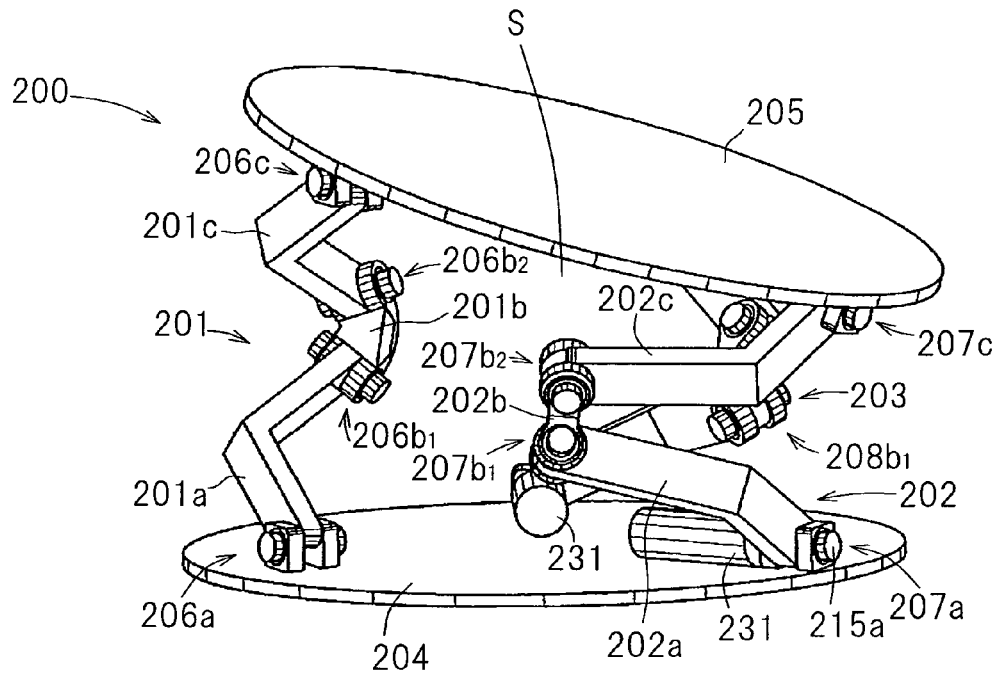
FIG. 19 is a perspective view showing a different example of the link actuating device according to the tenth embodiment of the present invention.

FIGS. 18 and 19 illustrate an example of the link actuating device 200 designed in accordance with the tenth preferred embodiment of the present invention, in which the link mechanism drive source 231 is mounted on the input member 204. In those examples, two link mechanism drive sources 231 are disposed and respective output shafts of those link mechanism drive sources 231 are connected coaxially with support rods 214a to 216a that are connected with the arm ends of the two end link members 201a and 203a on the input side. By controlling the respective rotational angle position of the end link members 201a to 203a with those link mechanism drive sources 231, the attitude of the remote controlled actuator 80 fitted to the output member 205 is controlled.

The link mechanism 201 to 203 of those link actuating device 200 employed in the practice of this embodiment of the present invention is of a mirror symmetry type and the input member 204 and the input side turning pair 206a to 208a and the output member 205 and the output side turning pair 206c to 208c are displaced towards a circumferential direction (a substantial distance in a widthwise direction) and the respective rotary shafts of the turning pairs $206b_1$ to $208b_1$ and $206b_2$ to $208b_2$ of the output side end link member 201c to 203c and the intermediate link member 201b to 203b are oriented towards the center axis of the input member 204. For this reason, even though the arm angle (the angle defined between respective axes at opposite arm ends of the end link member) is not 90°, the input side and the output side represent the geometrically same shape. As a result, interference between the intermediate link member 201b to 203b and the end link members 201a to 203a and 201c to 203c can be avoided. In particular, the example shown in FIG. 19 is such that the inner space S of the link mechanism 201 to 203 is large enough to facilitate installation of, for example, the link mechanism drive source 231 and the rotational angle detecting section (not shown), accompanied by such an advantage that the range of the center of gravity required for the stabilization can be expanded.

Figure 20:
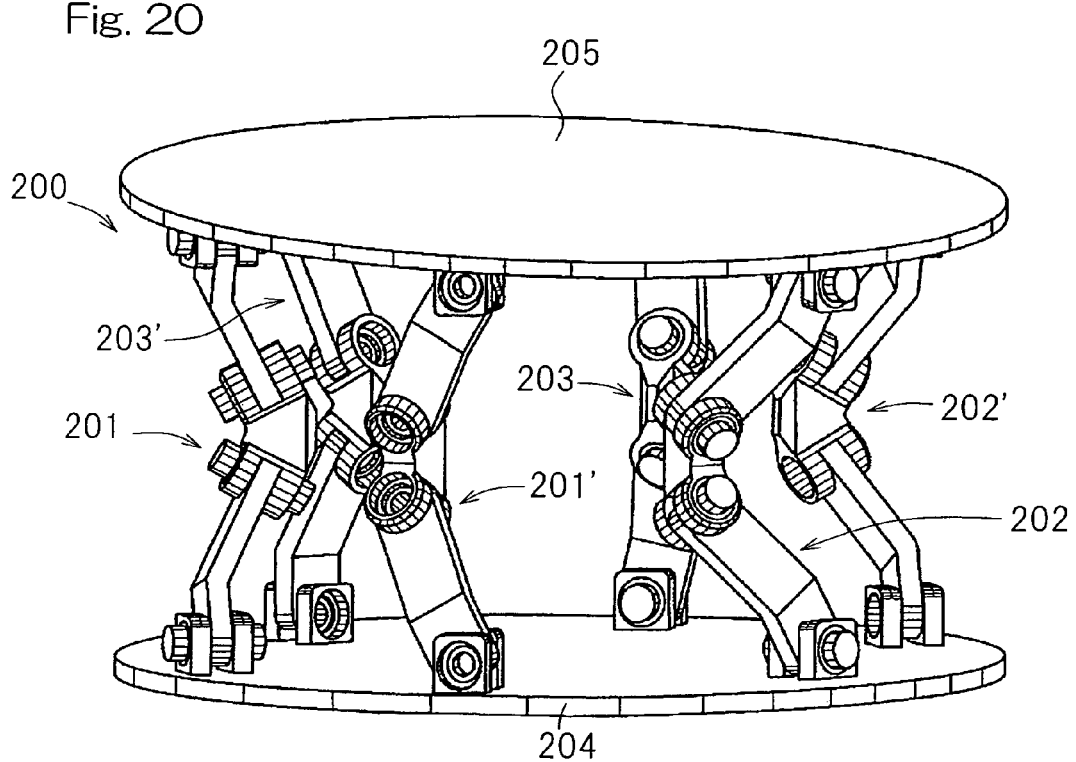
FIG. 20 is a perspective view showing the link actuating device employed in the remote controlled work robot according to an eleventh preferred embodiment of the present invention.

FIG. 20 illustrates an eleventh preferred embodiment of the present invention, in which the link actuating device 200 employed is comprised of six sets of link mechanisms 201, 202, 203, 201', 202' and 203' so that the range of the center of gravity for the stabilization can be expanded and also the rigidity can be increased.

Also, as another mode, a rotational angle sensor (not shown) may be provided in the support rod 214a to 216a, shown in FIG. 16, for supporting the input side end link member 201a to 203a. By so doing, no servo mechanism need be fitted to the link mechanism drive source 231 and, therefore, the link mechanism drive source 231 can be reduced in size and, also, no zero point setting is needed at the time the electric power is turned on.

The support rod 214a to 216a referred to previously is supported by a rotatable raceway ring of the bearing 217a to 219a and a stationary raceway ring of the bearing 217a to 219a is fixed to the support member 211a to 213a of the input member 204. The rotational angle sensor is comprises of a to-be-detected element, provided at an inner end of the support rod 214a to 216a, and a detecting element fitted to the input member 204 in face-to-face relation with this to-be-detected element. It is to be noted that although the to-be-detected element and the detecting element have been described as provided on a rotating side and on a stationary side, respectively, the detecting element and the to-be-detected element may be provided on the rotating side and the stationary side, respectively, since the to-be-detected element rotates merely about 45°.

The to-be-detected element referred to above is of a radial type and annual in shape and is comprised of, for example, an annular back metal, a magnetic generating member disposed on an outer peripheral side of the annular back metal and having a plurality of alternating magnetic poles N and S alternately magnetized thereto and is secured to the support rod 214a to 216a through the back metal. The magnetic generating member may be employed in the form of, for example, a rubber magnet bonded by vulcanization to the back metal and, also, this magnetic generating member may be of a type formed by a plastic magnet or a sintered magnet, in which case the back metal may not be necessarily essential.

The detecting element referred to above is comprised of a magnetic sensor of an alternate (full) magnetic field operating type capable of providing an rectangular output or a one-sided (half) magnetic field operating type capable of generating an output signal proportional to the magnetic flux density. This magnetic sensor is mounted on a magnetic detecting circuit substrate (not shown) and is molded with resin after having been inserted into a resinous casing together with the magnetic detecting circuit substrate. With the resinous casing fixed to the input member 204, the magnetic sensor and the magnetic detecting circuit substrate are fitted to the input member 204. The magnetic detecting circuit substrate is a substrate having a circuit surface mounted for the supply of an electric power to the magnetic sensor and also for processing an output signal of the magnetic sensor before it is outputted to the outside. It is recommended or sufficient to utilize the inner space S of the link mechanism 201 to 203 for wiring or the like.

Accordingly, when the to-be-detected element rotates incident to rotation of the support rod 214a to 216a, the detecting element generates an output signal corresponding to the magnetic flux density of the magnetic generating member, thus enabling the rotational angle of the support rod 214a to 216a, that is, the rotational angle of the end link member 201a to 203a to be detected. It is to be noted that the magnetic sensor forming the detecting element itself functions as an encoder capable of providing an A phase or Z phase output, but if a different magnetic sensor is provided other than the magnetic sensor, it is possible for it to function as an encoder capable of providing an AB phase output. Also, the to-be-detected element and the detecting element can employ a means of detecting the absolute rotational angle, a means such as disclosed in, for example, the JP Laid-open Patent Publication No. 2003-148999 or a means in which it is rendered to be a wire wound type detector such as, for example, an optical type or a resolver.

Figure 21:
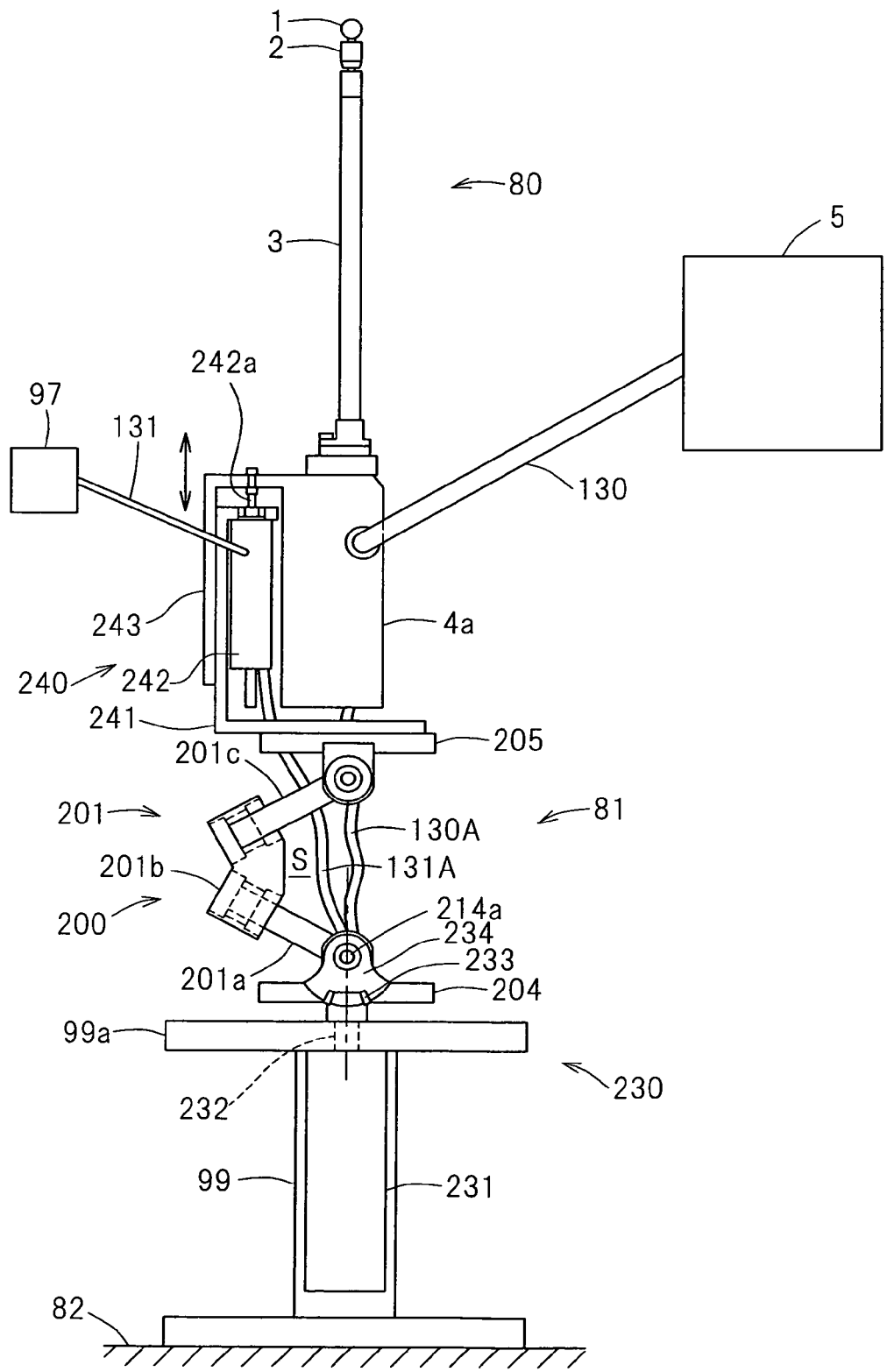
FIG. 21 is a diagram showing a schematic structure of the remote controlled work robot according to a twelfth preferred embodiment of the present invention, which robot is equipped with the support device comprised of, for example, the link actuating device.

The remote controlled work robot designed in accordance with a twelfth preferred embodiment of the present invention as shown in FIG. 21 is a modified example of the remote controlled work robot shown in and described with particular reference to FIG. 14. While the remote controlled work robot shown in and described with reference to FIG. 14 is such that the remote controlled actuator 80 is secured to the output member 205 of the link actuating device 200 through the mounting stand 90, the remote controlled work robot shown in FIG. 21 is such that the remote controlled actuator 80 is provided by a translatory mechanism 240 for linear movement in the same direction as the center axis of the link actuating device 200 relative to the output member 205 of the link actuating device 200. In other words, the support device 81 for this remote controlled work robot is made up of the link actuating device 200 and the translatory mechanism 240. Other structural features than those described above are similar to those shown in and described with reference to FIG. 14.

More specifically, the translatory mechanism 240 includes a reciprocating element 242a of a drive source 242 thereof which is connected with the drive unit housing 4a for the remote controlled actuator 80, after a motor mounting table 241 has been installed on the output member 205. The drive unit housing 4a is supported by the motor mounting table 241 through a translatory guide unit 243 so as to be movable in a direction along the direction of selective advance or retraction of the reciprocating element 242a of the drive source 242. Although the drive source 242 shown is a linear motor, it may be a rotary motor.

According to the foregoing construction, not only the position and the attitude of the remote controlled actuator 80 be altered by the link actuating device 200, but the position of the remote controlled actuator 80 in the direction of the center axis of the link actuating device 200 is altered by the translatory mechanism 240. The link actuating device 200 alters the position of the output member 205 on the trajectory which depicts a generally elliptical sphere because of its mechanism. For this reason, when the remote controlled actuator 80 is desired to be altered in position in the direction of the center axis of the link actuating device 200, the positioning is difficult because it accompanies a movement in a direction different from the direction of the center axis, and, also, there is a likelihood that a region of movement in the direction of the center axis will become short depending on the manner of use. However, the positional alteration by the translatory mechanism 240 is concurrently used, the positioning of the link actuating device 200 in the direction of the center axis can be facilitated and a sufficient range of movement can be obtained and, therefore, a meticulous processing with the tool 1 can be accomplished accurately.

The drive source 242 for the translatory mechanism 240 is controlled by the support device controller 97 for the one-degree-of-freedom system. A wiring connecting between the drive source 242 and the support device controller 97 is provided through the inner space S of the link mechanism 201 to 203 in a manner similar to the wiring 130 used to connect between the remote controlled actuator 80 and the actuator controller 5. In the instance as shown in FIG. 21, the wiring 131 is shown as extending outside the inner space S for the purpose of convenience, the wiring 131 in practice is arranged at a position indicated by a reference numeral 131A. Thus, disposition of the wiring 131 through the inner space S is effective to facilitate disposition of the wiring 131 and the wiring 131 will not constitute any obstruction.

Figure 22:
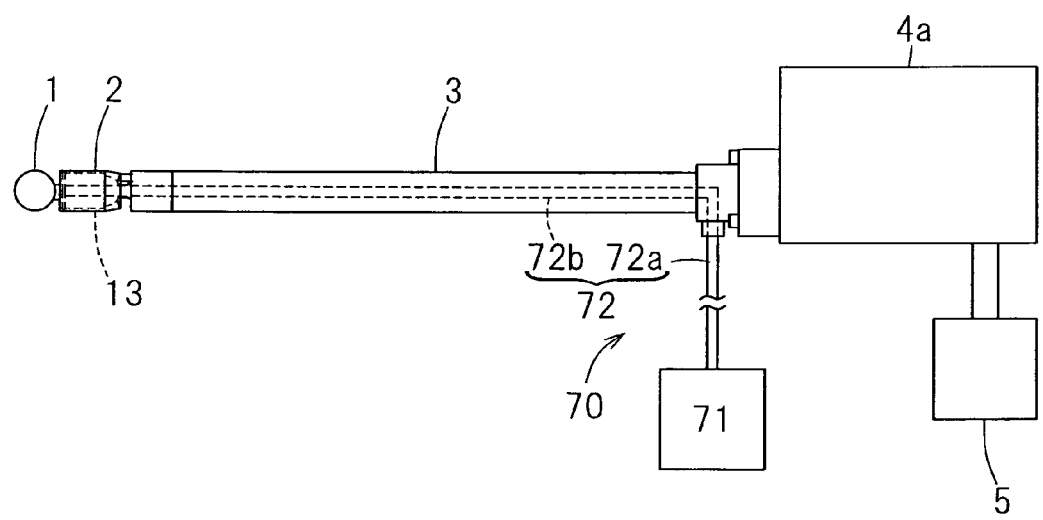
FIG. 22 is a diagram showing a schematic structure of the remote controlled work robot according to a thirteenth preferred embodiment of the present invention, which actuator is provided with a cooling section.

The remote controlled actuator 80 employed in the practice of the present invention can be provided with a cooling section 70 for cooling the tool 1 by taking advantage that the spindle guide section 3 has a hollow, in a manner as shown and described in connection with a thirteenth preferred embodiment of the present invention with particular reference to FIG. 22. Specifically, the cooling section 70 referred to above includes a cooling liquid supply device 71, provided outside the remote controlled actuator 80, and a cooling liquid supply tube 72 for supplying a cooling liquid from the cooling liquid supply device 71 towards the distal end side through the spindle guide section 3 and the interior of the distal end member 2, and the cooling liquid so supplied is discharged in an axial direction towards the tool 1 from the distal end of the distal end member 2. The cooling liquid supply tube 72 referred to above is comprised of an outer tube section 72a extending from the cooling liquid supply device 71 to the spindle guide section 3 and an inner tube section 72b extending through the spindle guide section 2 and the interior of the distal end member 2. Within the inner tube section 72b, the outer shell pipe 25 (as best shown in FIG. 3A) of the spindle guide section 3 and the housing 11 (also as best shown in FIG. 3A) for the distal end member 2 form the cooling liquid supply tube 72.

As the cooling liquid flows through the spindle guide section 3 and the interior of the distal end member 2, the rotary shaft 22, the rolling bearings 26 and 29 and the spindle 13 are cooled thereby. Those rotatable members tend to emit heat when rotated. Also, the tool 1 and the to-be-processed object are cooled by the cooling liquid discharged from the distal end member 2. Since in this way, the cooling liquid is passed through the spindle guide section 3 and the interior of the distal end member 2, no tube or piping for the supply of the cooling liquid need be provided outside and, therefore, the spindle guide section 3 and the distal end member 2 can be simplified and can be downsized in diameter. Where the flow of the cooling liquid to be passed through the outer shell pipe 25 is small, an extra cooling liquid may be supplied from outside to cool the tool 1 and the to-be-processed object. It is to be noted that the cooling liquid referred to above may be concurrently used to lubricate the rolling bearings 26 and 29. By so doing, the use of a grease, which is generally used in bearings, can be dispensed with and, moreover, no extra lubricating device may be employed. In the illustrated embodiment now under discussion, the tool 1 and the bearings 26 and 29, for example, have been described as cooled by the cooling section 70, but the cooling section 70 may be used to cool at least one of those component parts.

The cooling liquid referred to above is preferably in the form of either water or physiological saline. If the water or physiological saline is employed for the cooling liquid, the cooling liquid will not adversely affect the living body when the processing is performed with the distal end member 2 inserted into the living body. Where the water or physiological saline is employed for the cooling liquid, material for component parts that is exposed to and/or held in contact with the cooling water is preferably employed in the form of stainless steel excellent in resistance to corrosion. The other component parts forming the remote controlled actuator used in the practice of the present invention may be made of stainless steel.

FIGS. 23A and 23B illustrate the remote controlled actuator of a type employed in accordance with a fourteenth preferred embodiment of the present invention. The remote controlled actuator 80 shown therein includes two guide pipes 30 positioned within the outer shell pipe 25 and held at respective positions spaced 180° in phase from each other in a direction circumferentially thereof, and the attitude altering member 31 is reciprocally movably inserted within each of guide holes 30a which are inner diametric holes in the guide pipes 30. Between the two guide pipes 30 and 30, a plurality of reinforcement shafts 34 are arranged on the same pitch circle C as that of the guide pipes 30. No elastic restoring member 32 is provided. The guide faces F1 and F2 are each a spherical surface having a center of curvature at O or a cylindrical surface having a longitudinal axis aligned with the X-axis passing the point O.

The drive unit 4 (not shown) is provided with two attitude alteration drive sources 42 (also not shown) for individually reciprocally operating respective attitude altering members 31 and, by driving those two attitude alteration drive sources 42 in reverse directions relative to each other, the attitude of the distal end member 2 is altered. By way of example, if the upper attitude altering member 31 is first advanced towards the distal end side and the lower attitude altering member 31 is retracted as viewed in FIG. 23A, the housing 11 for the distal end member 2 is pressed by the upper attitude altering member 31, with the consequence that the distal end member 2 alters its attitude along the guide faces F1 and F2 so that, as viewed in FIG. 23A, the distal end side of the distal end member 2 may be oriented downwards. If both of the attitude altering members 31 are advanced and retracted in a direction reverse to that described above, the housing 11 for the distal end member 2 is pressed by the lower attitude altering member 31, with the consequence that the distal end member 2 alters its attitude along the guide faces F1 and F2 so that, as viewed in FIG. 23A, the distal end side of the distal end member 2, may be oriented upwards. At this time, pressures from the upper and lower attitude altering members 31 and a reactive force from the detent member 21 act on the distal end member coupling structure 15 and depending on the balance of those working forces the attitude of the distal end member 2 is determined. In this construction, since the housing 11 for the distal end member 2 is applied a pressure by those two attitude altering members 31, as compared with the embodiment shown in and described with particular reference to FIGS. 3A to 3C in which the pressure is applied only from the single attitude altering member 31, the attitude stability of the distal end member 2 can be increased.

Figure 24A:
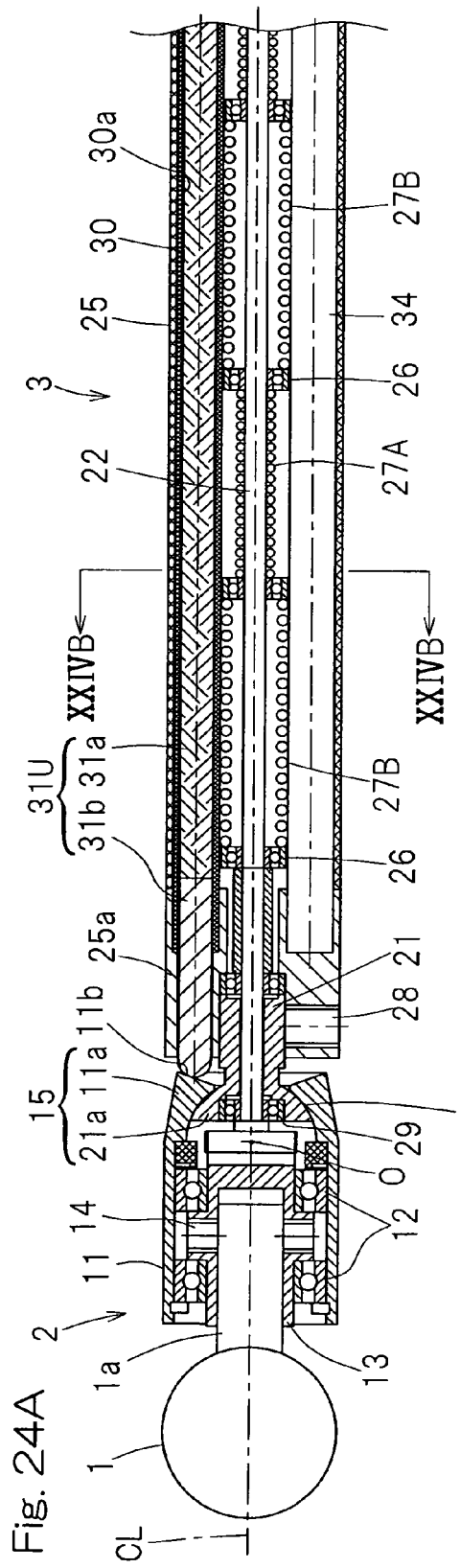
FIG. 24A is a sectional view showing the distal end member and the spindle guide section, both employed in the remote controlled actuator according to a fifteenth preferred embodiment of the present invention.
Figure 24B:
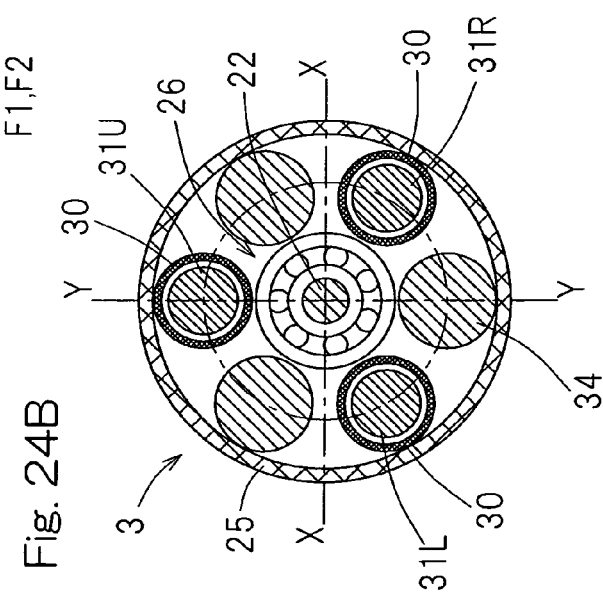
FIG. 24B is a cross sectional view taken along the line XXIVB-XXIVB in FIG. 24A.

FIGS. 24A and 24B illustrate the remote controlled actuator of a type employed in accordance with a fifteenth preferred embodiment of the present invention. The remote controlled actuator 80 shown therein includes three guide pipes 30 positioned within the outer shell pipe 25 and held at respective positions spaced 120° in phase from each other in a direction circumferentially thereof, and the attitude altering member 31 (31U, 31L and 31R) is reciprocally movably inserted within each of guide holes 30a which are inner diametric holes in the guide pipes 30. A plurality of reinforcement shafts 34 are arranged on the same pitch circle C as that of the guide pipes 30 in a fashion alternating the guide pipes 30. The guide faces F1 and F2 are each a spherical surface having a center of curvature as at O and the distal end member 2 is capable of being tilted in an arbitrary direction.

Figure 25A:
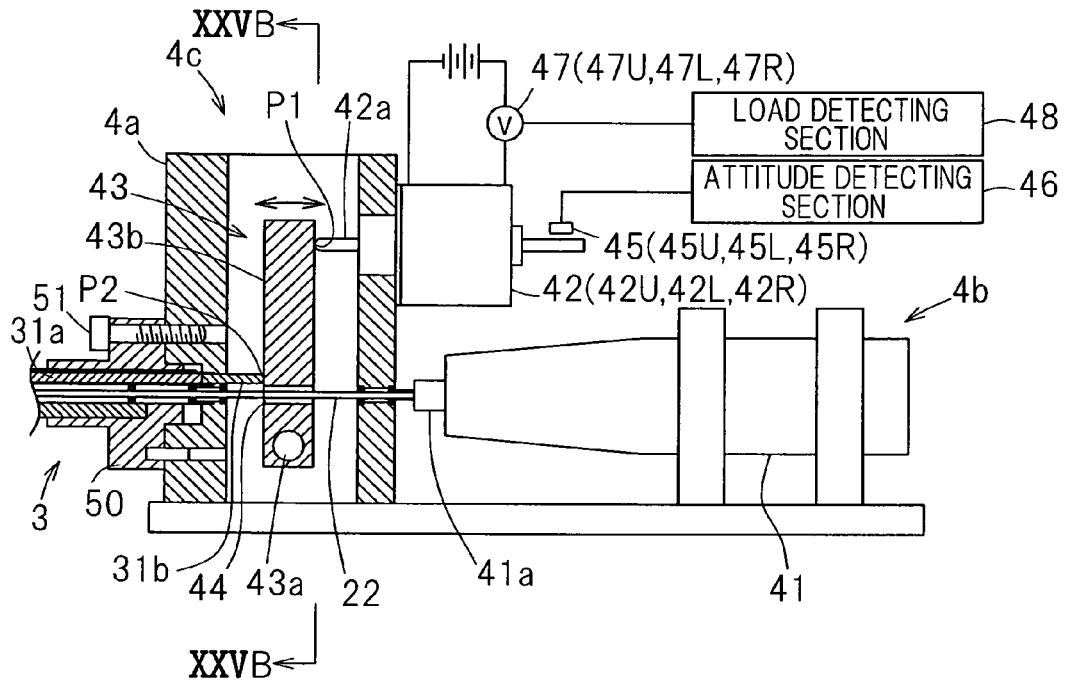
FIG. 25A is a sectional view showing the tool rotation drive mechanism and the attitude alteration drive mechanism both employed in the remote controlled actuator.
Figure 25B:
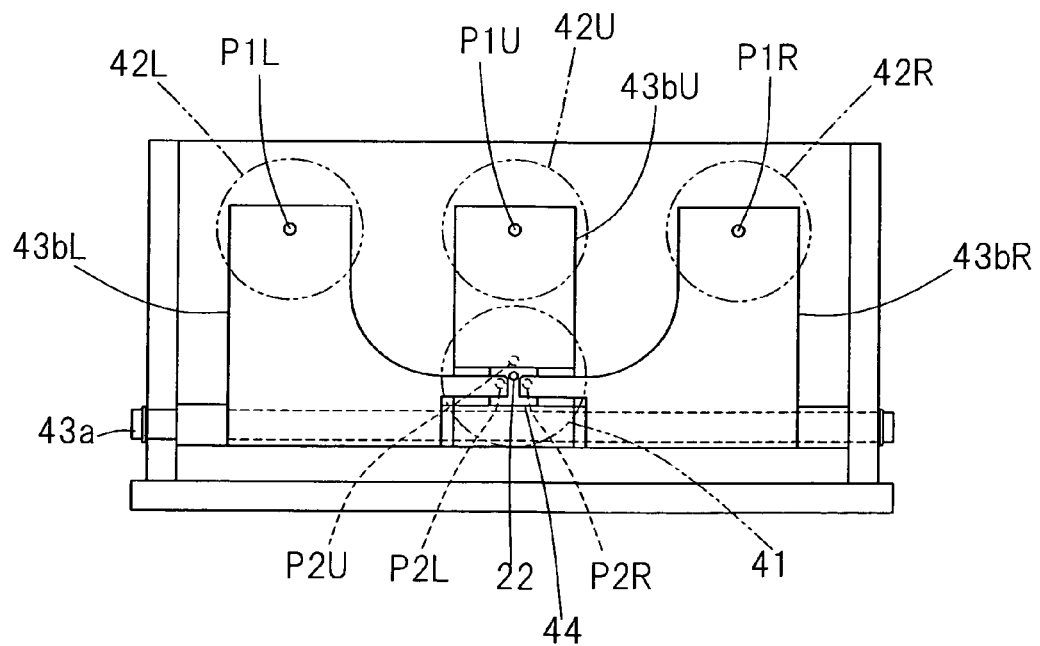
FIG. 25B is a cross sectional view taken along the line XXVB-XXVB in FIG. 25A.

FIGS. 25A and 25B illustrate the tool rotation drive mechanism 4b and the attitude alteration drive mechanism 4c both employed in the remote controlled actuator 80 employed in the practice of the fifteenth embodiment of the present invention referred to above. The tool rotation drive mechanism 4b is identical in structure with that shown in and described with reference to FIGS. 4A and 4B. However, three attitude alteration drive sources 42 (42U, 42L and 42R) are employed one for each attitude altering member 31 (31U, 31L and 31R). Movement of the output rod 42a of each of the attitude alteration drive sources 42 is transmitted to the corresponding attitude altering member 31 through a respective force increasing and transmitting mechanism 43. The force increasing and transmitting mechanism 43 makes use of a pivotable lever 43b (43bU, 43bL and 43bR) independently rotatable about the support pin 43a. Also, each of the attitude alteration drive sources 42 (42U, 42L and 42R) is provided with an actuating amount detector 45 (45U, 45L and 45R) for detecting the actuating amount of the attitude alteration drive source 42 and a supplied power meter 47 (47U, 47L and 47R) for detecting the amount of electric power supplied to the respective attitude alteration drive source 42.

When during the use the three attitude alteration drive sources 42 (42U, 42L and 42R) are driven to advance and retract the attitude altering members 31 (31U, 31L and 31R) in unison with each other, respectively, the attitude of the distal end member 2 is altered by remote control. For example, if the upper attitude altering member 31U as viewed in FIG. 24A is advanced towards the distal end side while the other two attitude altering members 31L and 31R are retracted, the housing 11 for the distal end member 2 is pressed by the upper attitude altering member 31U, with the consequence that the distal end member 2 is altered in attitude along the guide faces F1 and F2 with its distal end side oriented downwards. At this time, each of the attitude alteration drive sources 42 is controlled so that the amounts of advance and retraction of the respective attitude altering members 31 may become proper. If the attitude altering member 31 is conversely advanced and retracted, the housing 11 for the distal end member 2 is pressed by the left and right attitude altering members 31L and 31R and, accordingly, the distal end member 2 is altered in attitude along the guide faces F1 and F2 so that the distal end side thereof as viewed in FIG. 24A may be oriented upwards.

Also, if, while the upper attitude altering member 31U is halted, the left attitude altering member 31L is advanced towards the distal end side and the right attitude altering member 31R is retracted, the housing 11 for the distal end member 2 is pressed by the left attitude altering member 31L and, accordingly, the distal end member 2 is altered in attitude along the guide faces F1 and F2 so as to be oriented rightwards, that is, towards a side which is a rearwardly orientation of the sheet of FIG. 24A. On the other hand, if the left and right attitude altering members 31L and 31R are conversely advanced and retracted, the housing 11 for the distal end member 2 is pressed by the right attitude altering member 31R and, accordingly, the distal end member 2 is altered in attitude along the guide faces F1 and F2 so as to be oriented leftwards.

The use of the attitude altering member 31 at the three circumferential locations is effective to alter the attitude of the distal member 2 in one of directions of two axes (X-axis and Y-axis), upwards, downwards, leftwards and rightwards. At this time, respective pressures from the three attitude altering members 31 and a reactive force from the detent member 21 act on the distal end member coupling structure 15 and, depending on the balance of those working forces, the attitude of the distal end member 2 is determined. In this construction, since the housing 11 for the distal member 2 is pressed, the attitude stability of the distal end member 2 is high.

Figure 26A:
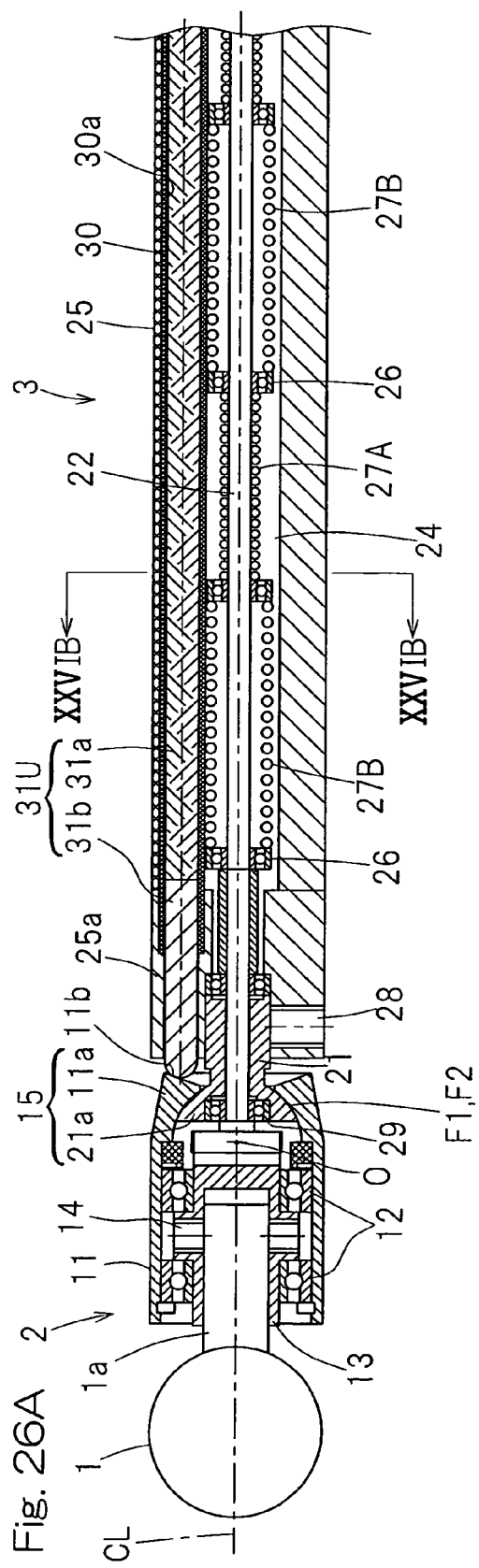
FIG. 26A is a sectional view showing the distal end member and the spindle guide section, both employed in the remote controlled actuator according to a sixteenth preferred embodiment of the present invention.
Figure 26B:
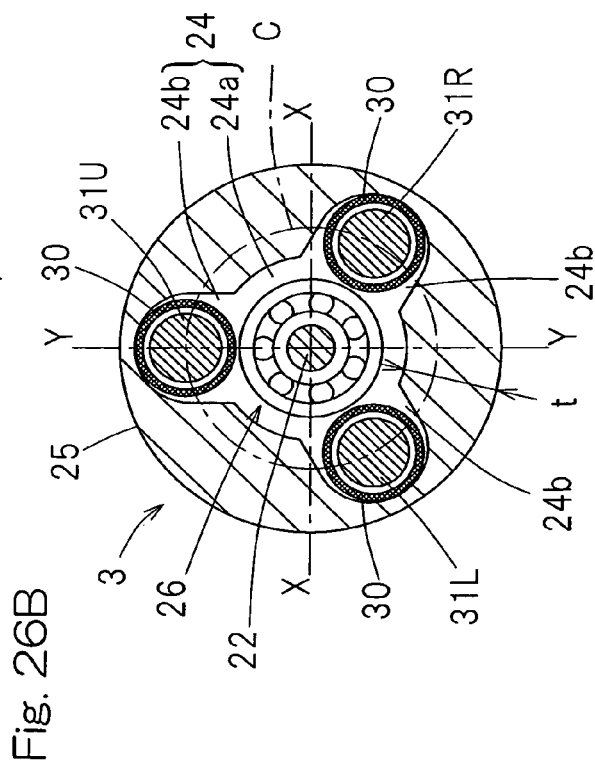
FIG. 26B is a cross sectional view taken along the line XXVIB-XXVIB in FIG. 26A.

FIGS. 26A and 26B illustrate the remote controlled actuator employed in the practice of a sixteenth embodiment of the present invention. The spindle guide section 3 employed in the remote controlled actuator 80 shown therein is such that the hollow 24 of the outer shell pipe 25 is comprised of a round hole portion 24a at a center portion, and three groove portions 24b that are depressed radially outwardly from respective circumferential positions on an outer periphery of the round hole portion 24a, which positions are spaced 120° in phase from each other. A peripheral wall at a tip of each of the groove portions 24b represents a semicircular section. And, the rotary shaft 22 and the rolling bearings 26 are accommodated within the round hole portion 24a and the attitude altering members 31 (31U, 31L and 31R) are accommodated within the respective groove portions 24b.

Because the outer shell pipe 25 is so designed and so configured as to have the above described sectional shape, the outer shell pipe 25 has an increased wall thickness t except for wall portions thereof aligned with the respective groove portions 24b and, therefore, the geometric moment of inertia of the outer shell pipe 25 increases. In other words, the rigidity of the spindle guide section 3 increased. Accordingly, not only can the positioning accuracy of the distal end member 2 be increased, but the cutting capability can also be increased. Also, positioning of the guide pipes 30 in the respective groove portions 24b makes it possible to facilitate the positioning of the guide pipes 30 in the circumferential direction and to provide a good assemblability.

The remote controlled actuator shown in FIGS. 27A to 27C and employed in the practice of a seventeenth preferred embodiment of the present invention is such that a radial groove 11c is formed in the base face 11b (best shown in FIG. 27C) of the housing 11 for the distal end member 2, and a spherical distal end of the attitude altering member 31 is held in abutment with a bottom surface of the groove 11c. The groove 11c and the attitude altering member 31 cooperate with each other to define a rotation preventing mechanism 37 and, accordingly, rotation of the distal end member 2 about the center line C of the spindle 13 relative to the spindle guide section 3 is effectively prevented when the distal end of the attitude altering member 31 then inserted in the groove 11*c* is engaged with a side face of the groove 11*c*.

The use of the rotation preventing mechanism 37 referred to above is effective to avoid the possibility that unintentional rotation of the distal end member 2 about the center line C may give rise to a hurt to a processing site or may result in damage to the distal end member 2 itself, when the distal end member 2 then holding the tool 1 becomes uncontrollable by reason of any trouble occurring in an attitude operation drive mechanism 4*c* (best shown in FIGS. 4A and 4B) for controlling the selective advance or retraction of the attitude altering member 31 or any other control device. It is to be noted that although only one attitude altering member 31 is shown in FIGS. 27A to 27C, the number of the attitude altering members may be plural and, even in such case, the foregoing description equally applies.

In describing each of the foregoing various preferred embodiments of the present invention, a portion of the base end face 11*b* of the housing 11 for the distal end member 2, which the attitude altering member 31 contacts, has been shown and described as defined by the inclined face which is closer towards the spindle guide section 3 on an outer diametric side thereof and which represents a linear shape in section. However, that portion of the base end face 11*b* of the housing 11 may be of a curved configuration in section, for example, an arcuate shape as shown in FIGS. 28A and 28B pertaining to an eighth preferred embodiment of the present invention. Depending on the case, without forming the base end face 11*b* of the housing 11 for the distal end member 2 to be the inclined face as described above, it may be a plane perpendicular to the direction of advance or retraction of the attitude altering member 31. It is to be noted that although FIGS. 28A and 28B illustrates the example in which only one attitude altering member 31 is employed, the number of the operating members used may be plural and in such case the foregoing description equally applied.

Also, in describing each of the foregoing various preferred embodiments of the present invention, the attitude altering member 31 has been shown and described as comprised of the wire 31*a* and the pillar shaped pins 31*b* at the opposite ends of the wire 31*a*. However, the use of the pillar shaped pins 31*b* may be dispensed with and only the wire 31*a* may be used for the attitude altering member 31. Also, in place of the wire 31 a, the attitude altering member 31 may be constituted by an array of pillar elements, which are relatively short in a lengthwise direction thereof, or spherical bodies (both not shown) arranged in a line.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. For example, although the present invention has been fully described as applied to the remote controlled work robot used in the medical field, the remote controlled work robot to which the present invention is applicable is not necessarily limited thereto and the present invention can be equally applied to the remote controlled work robot for use in any field other than the medical field. Where the remote controlled work robot of the present invention is to be used in mechanical processing such as, for example, a machining process, drilling of a hole of a curved configuration and cutting at a site deep in the groove can be accomplished.

Accordingly, such changes and modifications are, unless they depart from the scope of the present invention as delivered from the claims annexed hereto, to be construed as included therein.

REFERENCE NUMERALS

1 . . . Tool
2 . . . Distal end member
3 . . . Spindle guide section
4*a* . . . Drive unit housing
5 . . . Actuator controller
13 . . . Spindle
15 . . . Distal end member connecting structure
22 . . . Rotary shaft
26, 29 . . . Rolling bearing
30 . . . Guide pipe
30*a* . . . Guide hole
31 . . . Attitude altering member
41 . . . Tool rotation drive source
42 . . . Attitude alteration drive source
70 . . . Cooling section
80 . . . Remote controlled actuator
81 . . . Support device
81*a* . . . Three-degrees-of-freedom system
81*b* . . . Small sized multi-degree-of-freedom system
82 . . . Floor surface (Base)
84*b*, 87*a*, 89*a*, 96*a*, 242 . . . Drive source
91 . . . Support device controller for the 3-degrees-of-freedom mechanism
94 . . . Ceiling (Base)
97 . . . Support device controller for the 1-degree-of-freedom mechanism
98 . . . Support device controller for the small sized multi-degree-of-freedom mechanism
100 . . . Link actuating device
101, 102, 103 . . . Link mechanism
104 . . . Input member
105 . . . Output member
121 . . . Link mechanism drive source
130, 131 . . . Wiring
200 . . . Link actuating device
201, 202, 203 . . . Link mechanism
201', 202', 203' . . . Link mechanism
204 . . . Input member
205 . . . Output member
206*a*, 207*a*, 208*a* . . . Turning pair
206*b*$_1$, 207*b*$_1$, 208*b*$_1$ . . . Turning pair
206*b*$_2$, 207*b*$_2$, 208*b*$_2$ . . . Turning pair
206*c*, 207*c*, 208*c* . . . Turning pair
231 . . . Link mechanism drive source
240 . . . Translatory mechanism
S . . . Inner space

What is claimed is:
1. A remote controlled work robot comprising:
a remote controlled actuator; and
a support device to support the remote controlled actuator,
wherein the remote controlled actuator comprises
a spindle guide section of an elongated configuration;
a distal end member fitted to a distal end of the spindle guide section through a distal end member coupling structure for continuous alteration in attitude and rotatably supporting a spindle to hold a tool;

a drive unit housing connected with a base end of the spindle guide section, the spindle guide section being of a structure in which a rotary shaft to transmit a rotation of a tool rotation drive source, provided within the drive unit housing, to the spindle and an open ended guide hole are accommodated therein, and an attitude altering member to continuously alter the attitude of the distal end member when reciprocally moved with its distal end in engagement with the distal end member is reciprocally movably inserted within the guide hole; and an attitude alteration drive source to reciprocally move the attitude altering member is provided within the drive unit housing, wherein the support device comprises a single degree-of-freedom system, in which the remote controlled actuator has a degree of freedom in one direction, or a multi-degrees-of-freedom system, in which the remote controlled actuator has a two or more degrees of freedom relative to a base on which the support device is installed, and a drive source to operate a movable part of the degree-of-freedom system.

2. The remote controlled work robot as claimed in claim 1, further comprising a controller to control the remote controlled actuator and the support device by remote control.

3. The remote controlled work robot as claimed in claim 1, wherein the support device comprises the multi-degrees-of-freedom system, the multi-degrees-of-freedom system includes three or more sets of a link mechanisms, in each of which an end link member is connected for rotation relative to an input member, arranged on an input side, and an output member, arranged on an output side, and respective end link members on the input and output sides are connected for rotation relative to an intermediate link member;

with respect to a transverse section at a center portion of each of the link mechanisms, the input side and the output side are geometrically identical with each other; and of turning pair of each of the link mechanism connected with the input member, with respect to two or more sets of the link mechanisms, a link mechanism drive source to control arbitrarily the attitude of the output member is provided as the drive source.

4. The remote controlled work robot as claimed in claim 3, wherein the support device is such that the input member of the multi-degrees-of-freedom system thereof is connected with the base, and the output member is connected with the drive unit housing for the remote controlled actuator.

5. The remote controlled work robot as claimed in claim 3, wherein the support device is such that the input member of the multi-degrees-of-freedom system thereof is connected with the base and the output member is provided with a translatory mechanism to translationally move the movable part relative to a stationary part fixed to the output member, the movable part of the translatory mechanism being connected with the drive unit housing for the remote controlled actuator.

6. The remote controlled work robot as claimed in claim 3, further comprising:

a controller to control each of the remote controlled actuator and the support device by remote control; and a wiring to electrically connect between the remote controlled actuator and the controller, the wiring being passed within the three or more sets of the link mechanisms.

7. The remote controlled work robot as claimed in claim 5, further comprising:

a controller to control each of the remote controlled actuator and the support device by remote control; and a wiring to electrically connect between at least one of the remote controlled actuator and the translatory mechanism and the controller, the wiring being passed within the three or more sets of the link mechanisms.

8. The remote controlled work robot as claimed in claim 1, further comprising:

a bearing disposed within the spindle guide section to rotatably support the rotary shaft; and a cooling section to cool the bearing with a cooling liquid then flowing through the spindle guide section.

9. The remote controlled work robot as claimed in claim 8, wherein the cooling liquid is water or physiological saline.

10. The remote controlled work robot as claimed in claim 1, further comprising a tool cooling device to cool the tool with a cooling liquid then supplied to the outside or with a cooling liquid then flowing through the spindle guide section.

11. The remote controlled work robot as claimed in claim 10, wherein the cooling liquid is water or physiological saline.

12. The remote controlled work robot as claimed in claim 1, wherein the spindle guide section has a portion thereof curved.

* * * * *

UNITED STATES PATENT AND TRADEMARK OFFICE
CERTIFICATE OF CORRECTION

PATENT NO. : 8,316,961 B2
APPLICATION NO. : 13/317844
DATED : November 27, 2012
INVENTOR(S) : Hiroshi Isobe et al.

Page 1 of 1

It is certified that error appears in the above-identified patent and that said Letters Patent is hereby corrected as shown below:

Column 1, Line 7, Delete "U.S." and insert -- U.S.C. --, therefor.

Signed and Sealed this
Nineteenth Day of March, 2013

Teresa Stanek Rea
*Acting Director of the United States Patent and Trademark Office*